US006395395B1

(12) United States Patent
Hansen et al.

(10) Patent No.: US 6,395,395 B1
(45) Date of Patent: *May 28, 2002

(54) METHOD AND COMPOSITIONS FOR ENHANCING BLOOD ABSORBENCE BY SUPERABSORBENT MATERIALS

(75) Inventors: Michael R. Hansen, Seattle; Donald D. Halabisky, Tacoma, both of WA (US)

(73) Assignee: Weyerhaeuser Company, Federal Way, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/455,080

(22) Filed: Dec. 6, 1999

Related U.S. Application Data

(63) Continuation of application No. 08/675,803, filed on Jul. 5, 1996, which is a continuation of application No. 08/181,494, filed on Jan. 12, 1994, which is a continuation-in-part of application No. 07/931,059, filed on Aug. 17, 1992, now Pat. No. 5,543,215, which is a continuation-in-part of application No. 07/931,277, filed on Aug. 17, 1992, now Pat. No. 5,538,783, which is a continuation-in-part of application 07/931,213, filed on Aug. 17, 1992, now Pat. No. 5,300,192, which is a continuation-in-part of application No. 07/931,278, filed on Aug. 17, 1992, now Pat. No. 5,352,480, which is a continuation-in-part of application No. 07/931,284, filed on Aug. 17, 1992, now Pat. No. 5,308,896, which is a continuation-in-part of application No. 07/931,279, filed on Aug. 17, 1992, now Pat. No. 5,589,256, which is a continuation-in-part of application No. 08/107,469, filed on Aug. 17, 1993, now Pat. No. 5,672,418, which is a continuation-in-part of application No. 08/108,219, filed on Aug. 17, 1993, now Pat. No. 5,607,759, which is a continuation-in-part of application No. 08/107,467, filed on Aug. 17, 1993, now Pat. No. 5,693,411, which is a continuation-in-part of application No. 08/108,218, filed on Aug. 17, 1993, now Pat. No. 5,641,561, which is a continuation-in-part of application No. 08/153,819, filed on Nov. 15, 1993, now Pat. No. 5,447,997, which is a continuation-in-part of application No. 08/108,217, filed on Aug. 17, 1993, now Pat. No. 5,547,745.

(51) Int. Cl.$^7$ ............................................... B32B 5/02

(52) U.S. Cl. ................ 428/403; 428/296.1; 428/402; 428/408; 428/913; 604/365; 604/367; 604/368; 604/375

(58) Field of Search ................................. 428/402, 403, 428/408, 296.1, 913; 604/365, 368, 367, 375

(56) References Cited

U.S. PATENT DOCUMENTS 2,601,597 A   6/1952   Daniel, Jr. et al.
RE24,011 E   5/1955   Ericks (List continued on next page.)

FOREIGN PATENT DOCUMENTS

| CA | 729513 | 3/1966 |
| CA | 806352 | 2/1969 |
| CA | 813616 | 5/1969 |

(List continued on next page.)

OTHER PUBLICATIONS

Neogi et al., "Wet strength improvement via fiber surface modification," *Tappi*, 63:8 86–88 (Aug. 1980).

(List continued on next page.)

*Primary Examiner*—Terrel Morris
*Assistant Examiner*—Ula C. Ruddock

(57) ABSTRACT

The blood absorbence properties, e.g., free swell blood absorbence capacity and after load blood absorbence capacity of superabsorbent materials is enhanced by combining the superabsorbent materials with enhancing agents which serve to enhance the blood absorbent properties thereof. The enhancing agents can be applied to the superabsorbent materials or they can be provided on a fibrous material to be combined with the superabsorbent materials. The enhancing agents are selected from materials that include functionalities that allow them to hydrogen bond to the superabsorbent material when the enhancing agent is applied directly thereto or combined with materials to which the enhancing agents have been applied.

16 Claims, 4 Drawing Sheets

U.S. PATENT DOCUMENTS

| | | |
|---|---|---|
| 2,849,000 A | 8/1958 | Lewing |
| 2,953,187 A | 9/1960 | Francis, Jr. |
| 3,010,161 A | 11/1961 | Duvall |
| 3,059,313 A | 10/1962 | Harmon |
| 3,021,242 A | 12/1962 | Touey |
| 3,070,095 A | 12/1962 | Torr |
| 3,087,833 A | 4/1963 | Drelich |
| 3,327,708 A | 6/1967 | Sokolowski |
| 3,344,789 A | 10/1967 | Arnold et al. |
| 3,350,486 A | 10/1967 | Knoepfler et al. |
| 3,371,666 A | 3/1968 | Lewing |
| 3,377,302 A | 4/1968 | Gugliemelli et al. |
| 3,395,201 A | 7/1968 | Kalwaites |
| 3,409,497 A | 11/1968 | Roseland |
| 3,425,971 A | 2/1969 | Gugliemelli et al. |
| 3,494,992 A | 2/1970 | Wiegand |
| 3,521,638 A | 7/1970 | Parrish |
| 3,554,788 A | 1/1971 | Fechillas |
| 3,645,836 A | 2/1972 | Torr |
| 3,661,154 A | 5/1972 | Torr |
| 3,661,632 A | 5/1972 | Gagliardi et al. |
| 3,669,103 A | 6/1972 | Harper et al. |
| 3,670,731 A | 6/1972 | Harmon |
| 3,672,945 A | 6/1972 | Taylor |
| 3,686,024 A | 8/1972 | Nankee et al. |
| 3,692,622 A | 9/1972 | Dunning |
| 3,745,060 A | 7/1973 | Jumentier et al. |
| 3,758,641 A | 9/1973 | Zweigle |
| 3,766,922 A | 10/1973 | Krusko |
| 3,777,758 A | 12/1973 | Mesek et al. |
| 3,788,936 A | 1/1974 | Brock et al. |
| 3,804,092 A | 4/1974 | Tunc |
| 3,808,088 A | 4/1974 | Knechtges et al. |
| 3,886,941 A | 6/1975 | Duane et al. |
| 3,888,256 A | 6/1975 | Studinger |
| 3,888,257 A | 6/1975 | Cook et al. |
| 3,901,236 A | 8/1975 | Assarsson et al. |
| 3,903,889 A | 9/1975 | Torr |
| 3,908,659 A | 9/1975 | Wehrmeyer et al. |
| 3,923,592 A | 12/1975 | George et al. |
| 3,949,035 A | 4/1976 | Dunning et al. |
| 3,959,569 A | 5/1976 | Burkholder, Jr. |
| 3,978,257 A | 8/1976 | Ring |
| 3,991,237 A | 11/1976 | Ropfl et al. |
| 4,007,083 A | 2/1977 | Ring et al. |
| 4,009,313 A | 2/1977 | Crawford et al. |
| 4,035,217 A | 7/1977 | Kennette et al. |
| 4,051,086 A | 9/1977 | Reid |
| 4,055,180 A | 10/1977 | Karami |
| 4,061,268 A | 12/1977 | DeMaster |
| 4,062,451 A | 12/1977 | Gander |
| 4,066,583 A | 1/1978 | Spaulding |
| 4,071,636 A | 1/1978 | Nishino et al. |
| 4,096,312 A | 6/1978 | Holst et al. |
| 4,102,340 A | 7/1978 | Mesek et al. |
| 4,103,062 A | 7/1978 | Aberson et al. |
| 4,128,692 A | 12/1978 | Reid |
| 4,160,059 A | 7/1979 | Samejuna |
| 4,232,674 A | 11/1980 | Melican |
| 4,235,237 A | 11/1980 | Mesek et al. |
| 4,250,660 A | 2/1981 | Kitamura et al. |
| 4,282,121 A | 8/1981 | Goodrich |
| 4,289,513 A | 9/1981 | Brownhill et al. |
| 4,289,536 A | 9/1981 | Dereser |
| 4,324,706 A | 4/1982 | Tabe et al. |
| 4,332,917 A | 6/1982 | Heslinga et al. |
| 4,337,111 A | 6/1982 | Kauffmann et al. |
| 4,338,417 A | 7/1982 | Heslinga et al. |
| 4,354,487 A | 10/1982 | Oczkowski et al. |
| 4,364,992 A | 12/1982 | Ito et al. |
| 4,379,194 A | 4/1983 | Clarke et al. |
| 4,392,908 A | 7/1983 | Dehnel |
| 4,394,172 A | 7/1983 | Scheuble et al. |
| 4,404,250 A | 9/1983 | Clarke |
| 4,410,571 A | 10/1983 | Korpman |
| 4,412,036 A | 10/1983 | Pedersen et al. |
| 4,415,388 A | 11/1983 | Korpman |
| 4,424,247 A | 1/1984 | Erickson |
| 4,444,830 A | 4/1984 | Erickson |
| 4,457,978 A | 7/1984 | Wawzonek |
| 4,467,012 A | 8/1984 | Pedersen et al. |
| 4,481,076 A | 11/1984 | Herrick |
| 4,486,501 A | 12/1984 | Holbek |
| 4,492,729 A | 1/1985 | Bannerman et al. |
| 4,500,315 A | 2/1985 | Pieniak et al. |
| 4,507,438 A | 3/1985 | Obayashi et al. |
| 4,532,176 A | 7/1985 | Briggs et al. |
| 4,537,767 A | 8/1985 | Rothman et al. |
| 4,541,871 A | 9/1985 | Obayashi et al. |
| 4,552,816 A | 11/1985 | Spahic et al. |
| 4,558,091 A | 12/1985 | Hubbard |
| 4,597,930 A | 7/1986 | Szal |
| 4,605,401 A | 8/1986 | Chmelir et al. |
| 4,610,678 A | 9/1986 | Weisman et al. |
| 4,666,975 A | 5/1987 | Yamasaki et al. |
| 4,666,983 A | 5/1987 | Tsubakimoto et al. |
| 4,673,402 A | 6/1987 | Weisman et al. |
| 4,676,784 A | 6/1987 | Erdman et al. |
| 4,685,909 A | 8/1987 | Berg et al. |
| 4,699,808 A | 10/1987 | Menard et al. |
| 4,721,647 A | 1/1988 | Nakanishi et al. |
| 4,734,478 A | 3/1988 | Tsubakimoto |
| 4,755,178 A | 7/1988 | Insley et al. |
| 4,758,466 A | 7/1988 | Dabi et al. |
| 4,764,418 A | 8/1988 | Kuenn et al. |
| 4,772,492 A | 9/1988 | Bouchette |
| 4,788,080 A | 11/1988 | Hojo et al. |
| 4,798,744 A | 1/1989 | Goldstein et al. |
| 4,813,948 A | 3/1989 | Insley |
| 4,818,599 A | 4/1989 | Marcus |
| 4,824,689 A | 4/1989 | Kuenn |
| 4,826,880 A | 5/1989 | Lesniak et al. |
| 4,833,011 A | 5/1989 | Horimoto |
| 4,842,593 A | 6/1989 | Jordan et al. |
| 4,851,069 A | 7/1989 | Packard et al. |
| 4,874,811 A | 10/1989 | Borchers et al. |
| 4,886,697 A | 12/1989 | Perdelwitz, Jr. et al. |
| 4,888,238 A | 12/1989 | Katz et al. |
| 4,892,769 A | 1/1990 | Perdelwitz, Jr. et al. |
| 4,902,559 A | 2/1990 | Eschwey et al. |
| 4,902,565 A | 2/1990 | Brook |
| 4,944,734 A | 7/1990 | Wallach |
| 4,990,551 A | 2/1991 | Haubl |
| 5,002,814 A | 3/1991 | Knack et al. |
| 5,002,986 A | 3/1991 | Fujiura et al. |
| 5,041,101 A | 8/1991 | Seal |
| 5,057,166 A | 10/1991 | Young, Sr. et al. |
| 5,064,689 A | 11/1991 | Young, Sr. et al. |
| 5,128,082 A | 7/1992 | Makoui |
| 5,149,334 A | 9/1992 | Lahrman et al. |
| 5,149,335 A | 9/1992 | Kellenberger et al. |
| 5,161,686 A | 11/1992 | Weber et al. |
| 5,217,445 A | 6/1993 | Young et al. |
| 5,217,576 A | 6/1993 | Van Phan |
| 5,225,047 A | 7/1993 | Graef et al. |
| 5,225,095 A | 7/1993 | DiMaio et al. |
| 5,230,959 A | 7/1993 | Young, Sr. et al. |
| 5,240,562 A | 8/1993 | Phan et al. |
| 5,252,275 A | 10/1993 | Sultze et al. |
| 5,252,340 A | 10/1993 | Honeycutt |
| 5,264,082 A | 11/1993 | Phan et al. |

| | | |
|---|---|---|
| 5,278,206 A | 1/1994 | Gobel |
| 5,278,222 A | 1/1994 | Stack |
| 5,283,123 A | 2/1994 | Carter et al. |
| 5,294,249 A | 3/1994 | Luisi |
| 5,300,054 A | 4/1994 | Feist et al. |
| 5,300,192 A | 4/1994 | Hansen et al. |
| 5,308,896 A | 5/1994 | Hansen et al. |
| 5,312,522 A | 5/1994 | Van Phan et al. |
| 5,352,480 A | 10/1994 | Hansen et al. |
| 5,362,776 A | 11/1994 | Barenberg et al. |
| 5,378,528 A | 1/1995 | Makoui |
| 5,382,610 A | 1/1995 | Harada et al. |
| 5,384,179 A * | 1/1995 | Roe et al. .............. 428/192 |
| 5,432,000 A | 7/1995 | Young, Sr. et al. |
| 5,447,977 A | 9/1995 | Hansen et al. |
| 5,449,551 A | 9/1995 | Taniguchi |
| 5,492,759 A | 2/1996 | Eriksson |
| 5,498,478 A | 3/1996 | Hansen et al. |
| 5,516,569 A | 5/1996 | Veith et al. |
| 5,538,783 A | 7/1996 | Hansen et al. |
| 5,543,215 A | 8/1996 | Hansen et al. |
| 5,547,541 A | 8/1996 | Hansen et al. |
| 5,547,745 A | 8/1996 | Hansen et al. |
| 5,571,618 A | 11/1996 | Hansen et al. |
| 5,589,256 A | 12/1996 | Hansen et al. |
| 5,597,873 A | 1/1997 | Chambers et al. |
| 5,607,759 A | 3/1997 | Hansen et al. |
| 5,609,727 A | 3/1997 | Hansen et al. |
| 5,611,885 A | 3/1997 | Hansen et al |
| 5,614,570 A | 3/1997 | Hansen et al. |
| 5,633,316 A * | 5/1997 | Gartner et al. .......... 525/54.32 |
| 5,641,561 A | 6/1997 | Hansen et al. |
| 5,672,418 A | 9/1997 | Hansen et al. |
| 5,693,411 A | 12/1997 | Hansen et al. |
| 5,789,326 A | 8/1998 | Hansen et al. |
| 5,807,364 A | 9/1998 | Hansen |
| 5,851,672 A | 12/1998 | Wang et al. |
| 5,994,440 A | 11/1999 | Staples et al. |
| 5,998,032 A * | 12/1999 | Hansen et al. .............. 428/403 |

FOREIGN PATENT DOCUMENTS

| | | |
|---|---|---|
| CA | 841940 | 5/1970 |
| CA | 953 890 | 9/1974 |
| CA | 1052156 | 12/1976 |
| DE | 489 308 | 1/1930 |
| DE | 2 048 721 | 6/1971 |
| DE | 29 49 531 A1 | 7/1980 |
| DE | 3313344 | 10/1984 |
| DE | 1 079 796 | 6/1992 |
| EP | 0 071 063 A1 | 2/1983 |
| EP | 0 096 976 A2 | 12/1983 |
| EP | 0 099 586 A3 | 2/1984 |
| EP | 0 122042 A2 | 10/1984 |
| EP | 156649 A2 | 10/1985 |
| EP | 0157960 | 10/1985 |
| EP | 0 157 960 A1 | 10/1985 |
| EP | 0 210 754 A1 | 2/1987 |
| EP | 0233067 A2 | 9/1987 |
| EP | 317106 A2 | 5/1989 |
| EP | 366968 | 5/1989 |
| EP | 0402650 A2 | 12/1990 |
| EP | 0 427 316 A2 | 5/1991 |
| EP | 0 427 317 A2 | 5/1991 |
| EP | 0 429 112 A2 | 5/1991 |
| EP | 0 440 472 A1 | 8/1991 |
| EP | 0 442 185 A1 | 8/1991 |
| EP | 0450922 A2 | 10/1991 |
| EP | 0450924 A2 | 10/1991 |
| EP | 04509623 A2 | 10/1991 |
| EP | 471 114 A 2 | 2/1992 |
| EP | 0 509 708 A1 | 10/1992 |
| FR | 1 382 716 | 2/1964 |
| FR | 2080724 | 2/1971 |
| GB | 254357 | 7/1926 |
| GB | 260935 | 11/1926 |
| GB | 720390 | 12/1954 |
| GB | 1 217 452 | 12/1969 |
| GB | 1331964 | 9/1973 |
| GB | 2 004 201 A | 3/1979 |
| GB | 2004201 | 3/1979 |
| GB | 2 007 998 A | 5/1979 |
| GB | 2 092 895 A | 8/1982 |
| GB | 2119384 A | 11/1983 |
| GB | 2189127 | 10/1987 |
| JP | 58-25499 | 5/1983 |
| JP | 58183754 | 10/1983 |
| JP | 59-189103 | 10/1984 |
| JP | 60-7490 | 2/1985 |
| JP | Sho 61-28422 | 2/1986 |
| JP | 61270205 | 12/1986 |
| JP | 61-282465 | 12/1986 |
| JP | 42994/88 | 2/1988 |
| JP | 63035803 | 2/1988 |
| JP | 1-156578 | 6/1989 |
| JP | 1-162874 | 6/1989 |
| JP | 1229881 | 9/1989 |
| JP | 1-282389 | 11/1989 |
| JP | 2530668 | 6/1996 |
| JP | 3016879 | 12/1999 |
| SU | 1390284 | 4/1988 |
| WO | WO 88/01316 | 2/1988 |
| WO | WO 88/04704 | 6/1988 |
| WO | WO 88/07381 | 10/1988 |
| WO | WO 90/09236 | 8/1990 |
| WO | WO 90/11181 | 10/1990 |
| WO | WO/91/05108 | 4/1991 |
| WO | WO 91/09916 | 7/1991 |
| WO | WO 91/10010 | 7/1991 |
| WO | WO 93/24153 | 12/1993 |
| WO | WO 94/04351 | 3/1994 |
| WO | WO 94/04352 | 3/1994 |
| WO | WO 95/00703 | 1/1995 |

OTHER PUBLICATIONS

Amosov et al., "Aluminum hydroxy compounds—binders for dry–process paper," *Izv. VUZ, Lesnoi Zh.*, 6:72–76 (1986)IDS.

Blanchard and Reihart, "Dyeing of Crosslinked Cotton Containing Glycol Additives," *U.S. Dept. of Agriculture*, New Orleans, 24:13–17 (Jan. 1992).

Burkholder, "Absorbent Polymers—A New Concept in Fluid Absorption," *The Dow Chemical Company Designed Products Laboratory*, Midland, Michigan, pp. 73–79 (1973).

Byrd, "How bonds develop during web consolidation," *PTI*, pp. 240–243 (Oct. 1986).

Gorbushin et al., "Investigation of the effect of the nature and concentration of binders on the properties of dry–process paper," *Sb. Tr. Tsentr. Nauch.–Issled. Inst. Bumagi*, 9:117–123 (1974).

Gugliemelli et al., "Base–Hydrolyzed Starch–Polyacrylonitrile (S–PAN) Graft Copolymer. S–PAN–1:1, PAN M.W. 794,000*", *J. of Applied Copolymer Science*, 13:2007–2017 (1969).

Hoque et al., "Granulation and Tabletting of Iron Oxide–Chromic Oxide Catalyst Mass with the Aid of Binding Ingredients Part II–Cellulosic Derivatives and Polytehylene Glycol as Binding Ingredients,"*Fertilizer Technology*, 20:30–35 (1983).

Lindsay, "Absorbent Starch Based Co–polymers—Their Characteristics and Applications, " *Formed Fabrics Industry*, pp. 20, 24 and 26 (May 1977).

Lysogorskaya et al., "Effect of Moisture Content on the Development of Interfiber Bonds in Air–Laid Paper," *Leningrad Technological Institute of the Pulp and Paper Industry*, Zh. Prikl, Khim., 63:(8) 1869–1872 (1990).

Lysogorskaya et al., "Effect of Moisture Content on Development of Interfiber Bonding in the Structure of Air–Dried Paper," *Plenum Publ. Corp.*, pp. 1730–1733 (1991).

Ogurtsov et al., "Effect of the modulus of elasticity of the binder on the properties of dry–process paper," *Sb. Tr. Tsentr. Nauch.–Issled. Inst. Bumagi*, 9:123–127 (1974).

S. Lammie, "Use of Glycerine as a Softener for Paper Products," *The World's Paper Trade Review*, p. 2050, Dec. 13, 1962.

Sliwiok and Kowalska, "Investigation of Self–Assocaiation of the Selected Glycols and Cellulose Sorbents," Microchemical Journal, 26:68–74 (Jan. 1992).

"Super slurpers: Time for change?," *Chemical Week*, pp. 21–22 Jul. 24, 1974.

Weaver et al., "Hydrolyzed Starch–Polyacylonitrile Graft Copolymers: Effect of Structure on Properties* ", *J. of Applied Polymer Science*, 15:3015–3024 (1971).

Weaver et al., "Highly Absorbent Starch–Based Polymer," *Northern Regional Research Laboratory, Agricultural Research Service*, U.S. Dept. of Agriculture, Peoria, Illinois, pp. 169–177, No Date Given.

* cited by examiner

FIG. 6
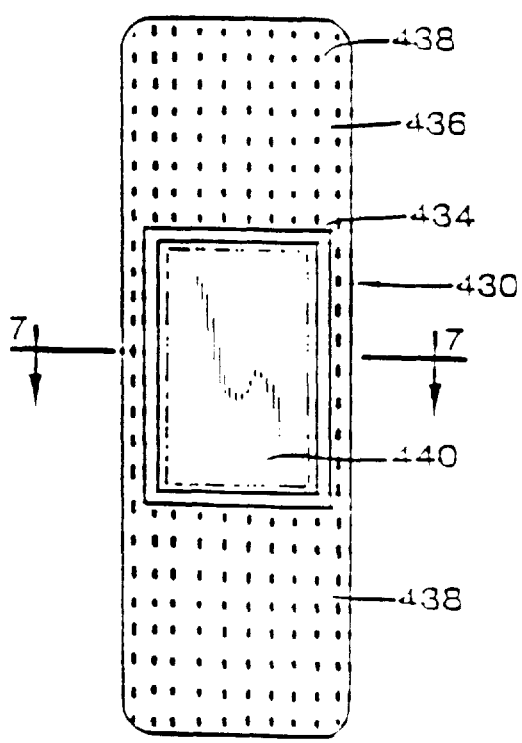
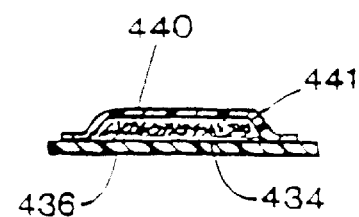
FIG. 7

METHOD AND COMPOSITIONS FOR ENHANCING BLOOD ABSORBENCE BY SUPERABSORBENT MATERIALS

CROSS REFERENCE TO RELATED APPLICATIONS

This is a continuation application of application Ser. No. 08/675,803 filed Jul. 5, 1996, which is a continuation of application Ser. No. 08/181,494, filed Jan. 12, 1994 which is a continuation-in-part application of the following U.S. patent applications, each of which was filed on Aug. 17, 1992, and each of which is hereby incorporated herein by reference: (1) Ser. No. 07/931,059, entitled POLYMERIC BINDERS FOR BINDING PARTICLES TO FIBERS, now U.S. Pat. No. 5,543,215; (2) Ser. No. 07/931,277, entitled NON-POLYMERIC ORGANIC BINDERS FOR BINDING PARTICLES TO FIBERS, now U.S. Pat. No. 5,538,783; (3) Ser. No. 07/931,213, entitled WET LAID FIBER SHEET MANUFACTURING WITH REACTIVATABLE BINDERS FOR BINDING PARTICLES TO FIBERS, now U.S. Pat. No. 5,300,192; (4) Ser. No. 07/931,278, entitled REACTIVATABLE BINDERS FOR BINDING PARTICLES TO FIBERS, now U.S. Pat. No. 5,352,480; (5) Ser. No. 07/931,284, entitled PARTICLE BINDERS FOR HIGH BULK FIBERS, now U.S. Pat. No. 5,308,896; (6) Ser. No. 07/931,279, entitled PARTICLE BINDERS THAT ENHANCE FIBER DENSIFICATION, now U.S. Pat. No. 5,589,256; and the following U.S. patent applications each of which was filed on Aug. 17, 1993 and each of which is hereby incorporated herein by reference: (7) Ser. No. 08/107,469, entitled PARTICLE BINDERS, now U.S. Pat. No. 5,672,418; (8) Ser. No. 08/108,219, entitled PARTICLE BINDING TO FIBERS, now U.S. Pat. No. 5,607,759; (9) Ser. No. 08/107,467, entitled BINDERS FOR BINDING WATER SOLUBLE PARTICLES TO FIBERS, now U.S. Pat. No. 5,693,411; (10) Ser. No. 08/108,217, entitled PARTICLE BINDERS, now U.S. Pat. No. 5,547,745; (11) Ser. No. 08/108,218, entitled PARTICLE BINDING TO FIBERS, now U.S. Pat. No. 5,641,561; and (12) application Ser. No. 08/153,819, filed Nov. 15, 1993 now U.S. Pat. No. 5,447,997.

FIELD OF THE INVENTION

The present invention relates to superabsorbent materials and compositions containing superabsorbent materials exhibiting enhanced blood absorbence properties and methods for enhancing the blood absorbence properties of such superabsorbent materials and compositions. More specifically, the present invention relates to superabsorbent materials exhibiting enhanced blood absorbence properties for use in disposable, superabsorbent products such as feminine hygiene articles and medical articles.

BACKGROUND OF THE INVENTION

Superabsorbent polymers have been developed in recent years that are capable of absorbing many times their own weight of liquid. These polymers, which are also known as water insoluble hydrogels, have been used to increase the absorbency of sanitary products, such as diapers and sanitary napkins. Superabsorbent polymers are often provided in the form of particulate powders, granules, or fibers that are distributed throughout superabsorbent cellulosic products to increase the absorbency of the product. Superabsorbent particles are described, for example, in U.S. Pat. Nos. 4,160,059; 4,676,784; 4,673,402; 5,002,814; and U.S. Pat. No. 5,057,166. Products such as diapers that incorporate superabsorbent hydrogels are shown in U.S. Pat. Nos. 3,669,103 and 3,670,731.

Superabsorbents have not found widespread use in superabsorbent sanitary articles, such as sanitary napkins, surgical wipes, and other articles used to absorb blood and other serous body fluids, because the superabsorbent materials do not absorb blood readily, nor do they have a high capacity for blood. The low blood absorbent capacity of the superabsorbent material means that large amounts of the superabsorbent material must be incorporated into blood absorbent articles, a factor which increases the production and materials cost for such superabsorbent articles.

U.S. Pat. Nos. 4,190,563 and 4,435,172 describe methods for improving the dispersability of particulate superabsorbent materials within blood. The '563 patent describes improving blood dispersability of superabsorbent materials by surface treating the material with one or more high molecular weight polyethers. The '563 patent describes that the polyethers can be used in amounts ranging from about 1% to about 35% by weight. The '563 patent describes that the polyether coated superabsorbent materials exhibited improved dispersability in blood. The '172 patent describes superabsorbent articles wherein the blood absorption rate is increased by the addition of amido compounds and non-ionic surfactants to water-soluble hydrophillic polymers. Such treated water-soluble hydrophillic polymers tend to be prone to potential risks of toxicity of the polymer and surfactants during use and after disposal (i.e., leaching of unused polymer or surfactant).

A superabsorbent for blood and serous body fluids is disclosed in U.S. Pat. No. 4,693,713. The disclosed superabsorbent composition includes component A, which is described as a water swellable synthetic or natural polymer or copolymer, and component B, which is described as an inorganic or organic compound that at normal temperature is present in the form of a pourable powder and is water soluble. The relatively high levels of component B described in the '713 patent contribute to processing, handling, use (from a toxicity standpoint) and disposal problems.

U.S. Pat. No. 4,381,784 describes an superabsorbent article for absorbing blood that includes a water soluble blood gelling agent to thicken and bind menstrual fluid within the superabsorbent article. According to the '784 patent, the blood gelling agents react with the protein present in blood or menstrual fluid, form particulate disordered structures according to the fourth class of gels defined by Flory, which are essentially completely water soluble, essentially completely linear, and which when placed in water will not form a Class 4 gel without the presence of blood protein. Such water soluble gelling agents are susceptible to the same risks as the water-soluble hydrophillic polymers discussed above with respect to the '784 patent.

U.S. Pat. No. 5,241,009 describes polycarboxyl group containing superabsorbents wherein neutralization of said carboxyl groups with potassium or lithium is described as providing a polymeric composition specifically adapted to absorb proteinaceous fluids, such as blood.

It would be advantageous to provide a superabsorbent material and composition which can be used in sanitary superabsorbent articles, such as sanitary napkins, and surgical wipes, which have a blood absorbent capacity and blood retention properties that would make them suitable choices for improving the blood absorbency of such articles. It would further be advantageous to provide such superabsorbent materials in a manner that is compatible with existing methods of producing such materials and incorporating them into absorbent articles. It would also be advantageous to provide such superabsorbent materials that do not suffer from the drawbacks of prior materials for absorbing serious fluids, such as blood.

SUMMARY OF THE INVENTION

The foregoing and other advantages are provided by the superabsorbent materials and compositions and methods of producing the superabsorbent materials and compositions in accordance with the present invention. Applicants have found that certain of the binders described in the earlier filed applications referenced above, when combined with superabsorbent materials as described below, surprisingly enhance the blood absorbence properties of the superabsorbent material and compositions containing the superabsorbent material and enhancing agents. The advantages of the present invention are obtained by providing superabsorbent materials in combination with enhancing agents that enhance the blood absorbence properties such as free swell blood absorbent capacity and after load blood absorbent capacities, of the superabsorbent materials, and compositions containing the same.

In accordance with the present invention, the enhancing agents can be provided with the superabsorbent materials in several ways, e.g., at least partially coating the superabsorbent material with the enhancing agent, at least partially embedding the enhancing agent in the superabsorbent material, or providing a mixture of superabsorbent material and a fibrous material at least partially coated with the enhancing agent. The enhancing agents can be polymeric enhancing agents, non-polymeric organic enhancing agents, or nonreactive combinations thereof with each other.

In one aspect of the present invention, when the polymeric enhancing agent is to be applied to the superabsorbent material, it includes enhancing agent molecules that have at least one functional group capable of forming a hydrogen bond or a coordinate covalent bond with the superabsorbent material. The enhancing agent is applied to the superabsorbent material to at least partially coat the superabsorbent material, and/or partially embed the enhancing agent in the superabsorbent material, and enhance the blood absorbence properties, such as free swell blood capacity and after load blood capacity, of the superabsorbent material.

In a preferred embodiment of this aspect of the present invention, the polymeric enhancing agent is present in an amount ranging from about 0.01% to about 3% of the weight of the superabsorbent material; more preferably about 0.01% to about 1.0% and the free swell blood absorbent capacity of the treated superabsorbent material is preferably at least 1.15 times, and more preferably at least 1.5 times the free swell blood absorbent capacity of the untreated superabsorbent material. In another preferred embodiment, the after load blood absorbent capacity of the treated superabsorbent material is preferably at least 1.15, and more preferably 1.5 times the after load blood absorbent capacity of the untreated superabsorbent material.

In still another preferred embodiment of this aspect of the present invention, the superabsorbent material includes superabsorbent particles that can be combined with a fibrous material to form an superabsorbent web or pad.

In accordance with this aspect of the present invention, the superabsorbent material treated with enhancing agent can be shipped to distribution points (for example, a customer's facility) where enhancing agent containing superabsorbent materials are further processed, e.g., combining with a fibrous material. Alternatively, the superabsorbent material treated with enhancing agent may be combined with a fibrous material by manufacturers of the fibrous material.

The polymeric enhancing agent may be selected from the group consisting of polyglycols [especially polyethylene glycol or poly(propyleneglycol)], a polycarboxylic acid, a polycarboxylate, a poly(lactone) polyol, such as diols, a polyamide, a polyamine, a polysulfonic acid, a polysulfonate and combinations thereof. Specific examples of some of these enhancing agents, without limitation, are as follows: polyglycols include polypropylene glycol (PPG) and polyethylene glycol (PEG); poly(lactone) polyols include poly (caprolactone) diol; polycarboxylic acids include polyacrylic acid (PAA); polyamides include polyacrylamide or polypeptides; polyamines include polyethylenimine and polyvinylpyridine; polysulfonic acids or polysulfonates include poly(sodium-4-styrenesulfonate) or poly(2-acrylamido-methyl-1-propanesulfonic acid); and copolymers thereof (for example a polypropylene glycol/polyethylene glycol copolymer). The polymeric enhancing agent typically has repeating units. The repeating unit may be the backbone of a compound, such as with a polypeptide, wherein the repeating polyamides occur in the peptide chain. The repeating unit may also refer to units other than those in the backbone, for instance a repeating acrylic acid unit. In such a case, the repeating units may be the same or different. In accordance with this aspect of the present invention, when the enhancing agent is applied to the superabsorbent material, the polymeric enhancing agent has a functional group capable of forming a hydrogen bond or a coordinate covalent bond with the superabsorbent material, and optionally, when the superabsorbent material is to be combined with a fibrous material, a functional group capable of forming a hydrogen bond with the fibrous material and, thus, binding the superabsorbent material to the fibrous material. At this time, a most preferred polymeric enhancing agent is polyethylene glycol.

In accordance with this aspect of the present invention, the non-polymeric enhancing agent has a volatility less than water, a functional group that is capable of forming a hydrogen bond or coordinate covalent bond with the superabsorbent material, and preferably where the superabsorbent material is to be combined with and bound to a fibrous material, a functional group that is capable of forming a hydrogen bond with the fibrous material. The non-polymeric enhancing agent is an organic enhancing agent, and preferably includes, without limitation, a functional group selected from the group consisting of a carboxyl (for example, carboxylic acids), a carboxylate, a carbonyl (for example, aldehydes), a sulfonic acid, a sulfonamide, a sulfonate, a phosphoric acid, a phosphoramide, a phosphate, an amide, an amine, a hydroxyl (such as an alcohol) and combinations thereof (for example, an amino acid or an hydroxy acid), wherein there is at least one functionality on the molecule selected from this group. Examples of such enhancing agents include polyols, polyamines (a non-polymeric organic enhancing agent with more than one amine group), polyamides (a non-polymeric organic enhancing agent with more than one amide group), polycarboxylic acids (a non-polymeric organic enhancing agent with more than one carboxylic acid functionality), polyaldehydes (a non-polymeric organic enhancing agent with more than one aldehyde), amino alcohols, hydroxy acids and other enhancing agents. These enhancing agents have functional groups that are capable of forming the specified bonds with the superabsorbent material and, when necessary and preferred, with the fibrous material.

More preferably, the non-polymeric organic enhancing agent is selected from the group consisting of glycerin, a glyceride monoester, a glycerin diester, ascorbic acid, urea, glycine, ammonium citrate, taurine (2-aminoethanesulfonic acid), dipropylene glycol, p-aminosalicylic acid, sorbitol, lactic acid, and combinations thereof. The preferred enhancing agents are non-polymeric molecules with a plurality of hydrogen bonding functionalities. Particularly preferred enhancing agents include those that can form five or six membered rings, most preferably six membered rings, with a functional group on the superabsorbent material surface. At present, glycerin, sorbitol, lactic acid, and combinations thereof are a particularly preferred enhancing agents.

In accordance with the present invention, the superabsorbent material treated with the polymeric or non-polymeric enhancing agent may or may not be combined with and/or bound to the fibrous material, although it is preferred from the standpoint of retention of superabsorbent material within an superabsorbent article. The fibrous material that the superabsorbent material is combined with may be natural fibers, such as cellulosic fibers or synthetic fibers. In one preferred embodiment, an superabsorbent product formed in accordance with the present invention includes a fibrous cellulosic mat that contains superabsorbent hydrogel particles in particulate form at least partially coated with enhancing agent and/or with enhancing agent at least partially embedded in its structure. Other superabsorbent materials such as superabsorbent granules and superabsorbent fibers may benefit from the treatment of the present invention. The superabsorbent particles are capable of forming hydrogen bonds or coordinate covalent bonds with the enhancing agent. The amount of enhancing agent present typically depends on a number of factors, including the nature of the enhancing agent and the superabsorbent particles. Hence, one skilled in the art will realize that the enhancing agent and the amount of enhancing agent suitable and particularly useful for a particular application will vary. However, the non-polymeric enhancing agent may suitably be present in an amount of from about 0.01% to 10% of the total weight of the superabsorbent materials, preferably from about 0.01% to 3%, and more preferably about 0.01% to 1%. When the nonpolymeric enhancing agent is used in accordance with this aspect of the present invention, the free swell blood absorbent capacity of the treated superabsorbent material is preferably at least 1.2 times, and more preferably at least double the free swell blood absorbent capacity of the untreated superabsorbent material. In another preferred embodiment, the after load blood absorbent capacity of the nonpolymeric enhancing agent treated superabsorbent material is preferably at least 1.2 times, and preferably at least double the after load blood absorbent capacity of the untreated superabsorbent material. If the superabsorbent particles of the present invention are present in a fibrous superabsorbent structure, they will be present in an amount of about 0.05% to 80% of the total weight of the fibrous material and the particles, preferably 1% to 80% or 3% to 80%, or more than 3% by weight. A particularly suitable range of particles is 5% to 70% by weight of the fibrous material and particles. An example of a suitable superabsorbent particle is a superabsorbent polymer, such as a starch-graft polyacrylate hydrogel fine or larger size particle, such as a granule, which is capable of forming hydrogen bonds with the enhancing agent.

The enhancing agent can be applied to the superabsorbent material in a number of ways, for example, by spraying the enhancing agent or agents onto the superabsorbent materials or slurrying or immersing them in the enhancing agent.

In a second aspect of the present invention, a blood absorbent composition of fibrous material and superabsorbent material is provided wherein the fibrous material has been at least partially coated with an enhancing agent, wherein combining the enhancing agent coated fibrous material with a superabsorbent material enhances the blood absorbent properties of the superabsorbent material and mixture, e.g., free swell blood absorbent capacity and after load blood absorbent capacity. As with the first aspect of the present invention summarized above, the enhancing agent may be either polymeric or nonpolymeric in nature and includes enhancing agent molecules.

In accordance with this aspect of the present invention, the polymeric enhancing agent may be selected from the group of polymeric enhancing agents summarized above with respect to the aspect wherein an enhancing agent is applied to the superabsorbent material. The polymeric enhancing agent molecules useful in this aspect have at least one functional group capable of forming a hydrogen bond coordinate covalent bond with the superabsorbent material.

The non-polymeric enhancing agent useful for application to the fibrous material in accordance with this aspect of the present invention has a volatility less than water. Suitable non-polymeric enhancing agent molecules have at least one functional group that is capable of forming a hydrogen bond or coordinate covalent bond with the superabsorbent material. The non-polymeric enhancing agent is an organic enhancing agent, and includes those non-polymeric organic enhancing agents summarized above with respect to the aspect of the present invention wherein an enhancing agent is applied to the superabsorbent material.

More preferably, in accordance with this aspect of the present invention, the organic non-polymeric enhancing agent is selected from the group consisting of glycerin, a glycerin monoester, a glycerin diester, ascorbic acid, urea, glycerin, ammonium citrate taurine (2-aminoethanesulfonic acid), p-aminosalicylic acid, dipropylene glycol, sorbitol, lactic acid, and combinations thereof. In accordance with this aspect of the present invention, particularly preferred enhancing agents include those that can form five or six membered rings, most preferably six membered rings, with a functional group on or close to the superabsorbent material surface. At present, glycerin, sorbitol, lactic acid, and combinations thereof are particularly preferred, with glycerin being more particularly preferred.

The fibrous material useful in accordance with this aspect of the present invention may be natural fibers, such as cellulosic or synthetic fibers. It has been found that whether the enhancing agent treated fibrous material and the superabsorbent material are combined, the superabsorbent material exhibits blood absorbence properties that are enhanced, and accordingly the mixture of superabsorbent material and treated fibrous material exhibit blood absorbence properties that are enhanced compared to a mixture of untreated fibrous material and the superabsorbent material. Accordingly, a superior superabsorbent composition is produced that has improved blood absorbent properties, such as free swell blood capacity and after load blood capacity.

In one preferred embodiment of this aspect of the present invention, an absorbent product comprises a fibrous cellulosic mat that contains superabsorbent hydrogel particles in particulate form. The superabsorbent particles are capable of forming hydrogen bonds or coordinate covalent bonds with the enhancing agent, depending upon the enhancing agent, while depending on its functionality the enhancing agent may form hydrogen bonds with the hydroxyl groups of the cellulose fibers. The amount of enhancing agent present typically depends on a number of factors, including the nature of the enhancing agent and superabsorbent particles. Hence, one skilled in the art will realize that the amount of enhancing agent suitable and particularly useful for a particular application will vary. However, the enhancing agent may suitably be present in an amount of from about 2% to 30% of the total weight of the fibrous material and enhancing agent. An especially suitable range of enhancing agent is about 2% to 15% of the total weight of the fibrous material and enhancing agent. The superabsorbent particles may suitably be present in an amount of about 0.05% to 80%, preferably about 1% to 80% or about 3% to 80%, or more than about 3% by weight of the total weight of the fibrous material and the particles. A particularly suitable range of particles is about 5% to 70% by weight of the fibrous material and particles. An example of a suitable particle is a superabsorbent polymer such as a starch graft polyacrylate hydrogel fine or larger size particle such as a granule. In a preferred embodiment of this aspect of the present invention, the after load blood absorbent capacity of a mixture of enhancing agent treated fibrous material and superabsorbent particles is at least 1.3 times the after low blood absorbent capacity of a mixture of untreated fibrous material and superabsorbent particles.

In especially preferred embodiments of this aspect of the present invention, the fibers are cellulosic and the particles are superabsorbent particles. The fibers may also be continuous or discontinuous synthetic or natural fibers.

When the preferred liquid enhancing agent is used (for example, glycerin or a solution of glycine powder), the fibers suitably contain at least about 0.5% water by weight. A solid enhancing agent is suitably used with fibers having less than 0.5% water by weight if the enhancing agent is heated above its melting point to liquefy it. The solid can be applied to the fibers as a hot saturated solution or the solid enhancing agent may be heated above its melting point to liquefy the enhancing agent, which is later applied to the fibers. The enhancing agent may be thermoplastic or meltable, such that it can be heated above its melting point/or softening point and then cooled to fuse fibers to each other. The thermoplastic properties of the enhancing agent can also provide mechanical adherence between the particles and fibers.

The present invention also is directed to absorbent products produced by any of the methods described herein, and to absorbent articles comprised of such absorbent products.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein:

FIG. 6 illustrates a plan view of a bandage incorporating particles with enhancing agent applied thereto and fibers in accordance with the present invention; and FIG. 7 is a sectional view of the bandage of FIG. 6, taken along line 7—7 of FIG. 6.

DETAILED DESCRIPTION OF THE PREFERRED EMBODIMENT

Figure 1:
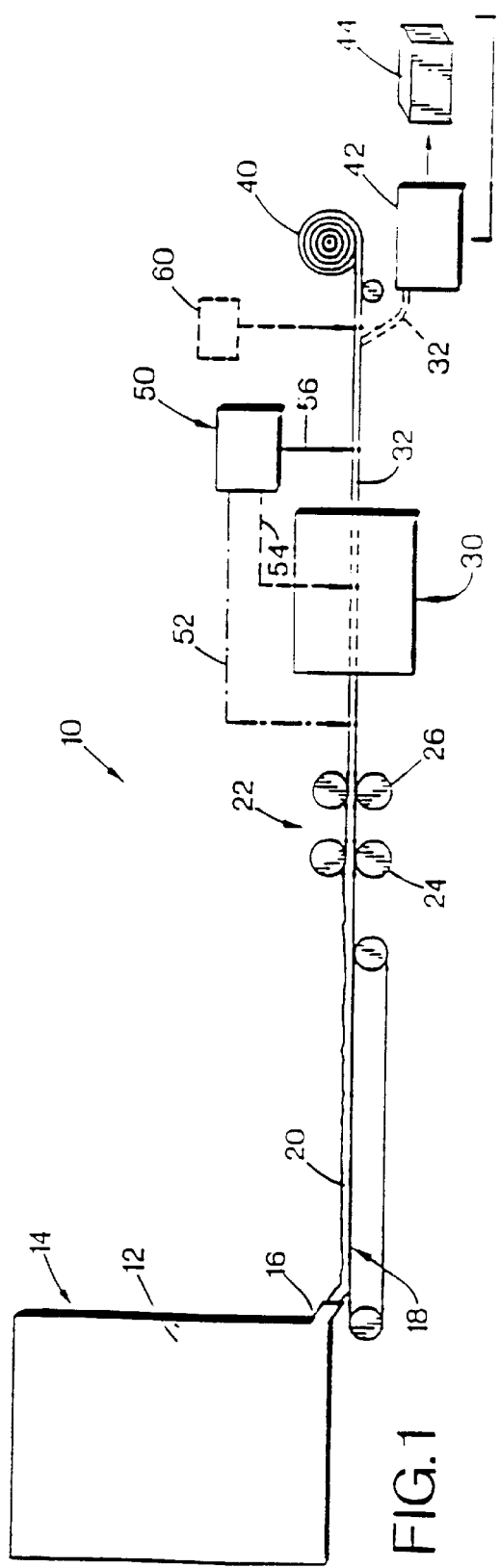
FIG. 1 is a schematic illustration of a wet laid sheet manufacturing line illustrating the application of enhancing agent coated particles in accordance with the present invention during the manufacture of a fibrous sheet.

In accordance with the present invention, applicants have discovered that superabsorbent material, when combined with enhancing agents as described below in more detail, enhance the blood absorbence properties, e.g., free swell blood capacity and after load blood capacity of the superabsorbent material. The enhancing agents useful in accordance with the present invention are preferably selected from materials that have been found to be useful as binders for binding particles to fibrous materials, as described in the U.S. patent applications referenced above. The following description will first describe a first aspect of the present invention wherein the enhancing agent is applied to a superabsorbent material, and then describe a second aspect of the present invention wherein the enhancing agent is applied to the fibrous material which is then combined with a superabsorbent material. The following description refers to wood pulp fibers such as cellulose fibers and superabsorbent particles for purposes of clarity. It should be understood that wood pulp fibers and superabsorbent particles are representative of the fibrous materials and superabsorbent materials useful in accordance with the present invention.

Though not intended to be limited to the following theory, it is believed that the ability of the enhancing agents described herein to increase the blood absorbence properties of superabsorbent materials may result from at least partial bonding of the enhancing agent either on the surface or at least partially embedded into the surface of the superabsorbent material. Such bonding of the enhancing agents to the superabsorbent material is believed to "hold open" the absorbent matrix of the superabsorbent material and modify its hydrophilicity or hydrophobicity, thus allowing the superabsorbent material to readily absorb and retain serous bodily fluids such as blood.

I. Enhancing Agent on Superabsorbent Material

In accordance with this aspect of the present invention, enhancing agent is applied to superabsorbent materials in order to enhance the blood absorbence properties of the superabsorbent material. The application of the enhancing agent to the absorbent materials is described below in more detail. This aspect of the present invention is described below in the context of the manufacture of a product that includes superabsorbent material treated with an enhancing agent in accordance with this aspect of the present invention and a fibrous material. The product used for the following description is a mat of cellulose fibers combined with the superabsorbent material treated with enhancing agent.

A. Processing of Absorbent Materials

In a preferred embodiment the added superabsorbent material is superabsorbent particles, which comprise polymers that swell on exposure to water and form a hydrated gel (hydrogel) by absorbing large amounts of water. Superabsorbents are defined herein as materials that exhibit the ability to absorb large quantities of liquid, i.e., in excess of 10 to 15 parts of liquid per part thereof. These superabsorbent materials generally fall into three classes, namely starch graft copolymers, cross-linked carboxymethylcellulose derivatives and modified hydrophilic polyacrylates. Examples of such absorbent polymers are hydrolyzed starch-acrylonitrile graft copolymer, a neutralized starch-acrylic acid graft copolymer, a saponified acrylic acid ester-vinyl acetate copolymer, a hydrolyzed acrylonitrile copolymer or acrylamide copolymer, a modified cross-linked polyvinyl alcohol, a neutralized self-crosslinking polyacrylic acid, a cross-linked polyacrylate salt, carboxylated cellulose, and a neutralized cross-linked isobutylenemaleic anhydride copolymer. Once polymerized, whether by solution polymerization or by inverse phase polymerization, these materials are typically dried and ground. At this point, the materials may be treated with the enhancing agent in a variety of commercially available mixing devices.

B. Processing of Fibers

FIG. 1 illustrates a wet laid sheet manufacturing line such as a pulp sheet manufacturing line 10. In this manufacturing line, a pulp slurry 12 is delivered from a headbox 14 through a slice 16 and onto a Fourdrinier wire 18. The pulp slurry 12 typically includes cellulose fibers such as wood pulp fibers and may also include synthetic or other non-cellulose fibers as part of the slurry. Water is drawn from the pulp deposited on wire 18 by a conventional vacuum system, not shown, leaving a deposited pulp sheet 20 which is carried through a dewatering station 22, illustrated in this case as two sets of calendar rolls 24, 26 each defining a respective nip through which the pulp sheet or mat 20 passes. From the dewatering station, the pulp sheet 20 enters a drying section 30 of the pulp manufacturing line. In a conventional pulp sheet manufacturing line, drying section 30 may include multiple canister dryers with the pulp mat 20 following a serpentine path around the respective canister dryers and emerging as a dried sheet or mat 32 from the outlet of the drying section 30. Other alternate drying mechanisms, alone or in addition to canister dryers, may be included in the drying stage 30. The dried pulp sheet 32 has a maximum moisture content pursuant to the manufacturer's specifications. Typically, the maximum moisture content is no more than 10% by weight of the fibers and most preferably no more than about 6% to 8% by weight. Otherwise, the fibers tend to be too damp. Unless overly damp fibers are immediately used, these fibers are subject to degradation by, for example, mold or the like. The dried sheet 32 is taken up on a roll 40 for transportation to a remote location, that is, one separate from the pulp sheet manufacturing line, such as at a user's plant for use in manufacturing products. Alternatively, the dried sheet 32 is collected in a baling apparatus 42 from which bales of the pulp 44 are obtained for transport to a remote location.

An enhancing agent of the type explained in detail below is applied to superabsorbent particles, as described below, such as superabsorbent particles, and then the enhancing agent treated particles are applied to the pulp sheet from one or more particle applying devices, one of which is indicated at 50 in FIG. 1. Any enhancing agent applying device may be used for applying enhancing agent to the superabsorbent particles, such as sprayers, or immersion applicators or the like. Sprayers are typically easier to utilize and incorporate into a pulp sheet manufacturing line. The enhancing agent is applied to the particles and then the particles are deposited onto the pulp sheet. The enhancing agent also may be sprayed or otherwise applied to the particles as they fall or are otherwise deposited onto the sheet. As indicated by the arrows 52, 54 and 56, the enhancing agent treated particles may be applied at various locations or at multiple locations on the pulp sheet manufacturing line, such as ahead of the drying stage 30 (indicated by line 52), intermediate the drying stage 30 (as indicated by line 54), or downstream from the drying stage 30 (as indicated by the line 56). Particles with water-soluble enhancing agents, such as non-polymeric urea, are typically applied at a location where sufficient drying can still take place in the drying stage to produce a drier enhancing agent treated particle containing fiber sheet with no more than maximum desired moisture content. Consequently, to take advantage of the drying stage 30, particles with wet water-based enhancing agents may be applied at locations 52 or 54. If wet water-based enhancing agent containing particles are applied at location 56 in an amount which would cause the moisture content of the sheet to exceed the desired maximum level, an additional drying stage (not shown) may be included in the pulp manufacturing line to bring the moisture content down to the desired level.

Superabsorbent particles with a non-aqueous based enhancing agent, such as glycerin, would most preferably be added downstream from the drying stage at location 56 or during the drying stage as indicated by location 54. However, particles with liquid non-aqueous enhancing agents may also be added at a location, such as location 52, upstream of the drying stage. At this latter location, the water in the wet web at this point may tend to attract these enhancing agents into the mat or sheet as many of the enhancing agents tend to be hydroscopic. Since non-aqueous enhancing agents typically do not enhance the degradation of the product due to the addition of moisture to the sheet, particles with such enhancing agents can be applied downstream from the drying stage without bringing the moisture content of the sheet above the desired maximum level.

Again, the enhancing agent treated superabsorbent materials, selected as explained below, may be added to the sheet on the pulp manufacturing line. Another suitable absorbent material applicator is indicated at 60 and may comprise a bulk or volumetric metering device. These superabsorbent materials may be sprinkled, poured or otherwise added to the sheet.

Although the above approach is advantageous because the superabsorbent particles are incorporated into the fibers at a single processing site, during transportation of rolls or bales of these fibers it is possible for the particles to become dislodged by mechanical impact during transport. In addition, this approach interferes with the customization of the fiber application at a user's location. For example, a user may want the capability of selecting particular types or brands of superabsorbent particles for combination with the fibers in the user's products, without having this selection made by a pulp-sheet manufacturer who incorporates the particles into the pulp sheet during its manufacture. Also, certain particles may degrade over time, making it advantageous to add such particles immediately prior to incorporation into products. For example, some superabsorbent particles are susceptible for absorbing moisture from the atmosphere during shipment. Therefore, it is also advantageous to provide a fibrous product in which the end user of the product may incorporate the desired superabsorbent particles treated with enhancing agents in accordance with this aspect of the present invention at the time the fibers are converted into products.

Figure 2:
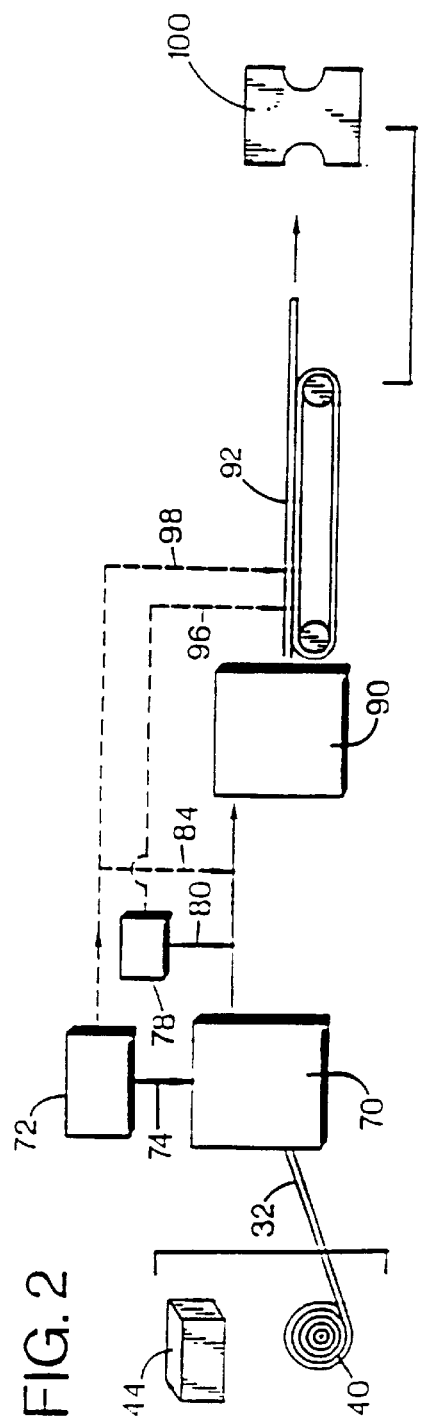
FIG. 2 is a schematic illustration of a web manufacturing line for combining enhancing agent coated particles and fibrous material in accordance with the present invention.

Therefore, in keeping with this latter preferred approach, as illustrated in FIG. 2, the respective rolls 40 or bales 44 of fibers, without particles, are transported to a remote location for use by a user. These rolls or bales (or otherwise transported fibers, e.g., bagged, containerized or otherwise in bulk form) are then refiberized by a fiberizing apparatus 70. Although any fiberizer may be used, a typical fiberizing apparatus 70 is a hammermill which may be used alone or in conjunction with other devices such as picker rolls or the like for breaking up the sheet 32 or bales 42 into individual fibers.

A particulate material adding mechanism 72 (e.g., like mechanism 60) delivers the desired enhancing agent treated particulate materials to the fibers at the desired location in the user's process. Again, the device 72 typically comprises a metering mechanism, although any suitable device for adding particulates to fibrous materials may be used. For example, the particulates may be delivered as indicated by line 74 to the fiberizing apparatus 70. Enhancing agent may also be combined with the particles as the particles are added to the fiber sheet. As yet another alternative, the fiberized fibers are delivered to an air-laying device 90 and reformed into a desired product such as a web indicated at 92. In addition, the enhancing agent treated particles may be applied to specifically defined locations on the web 92, such as in target zones of an absorbent core of a product, thereby minimizing the wasting of the superabsorbent material. A specific example of a target zone is the crotch region of a feminine napkin where most napkin wetting would occur. The application of superabsorbent particles to such a zone places these particles at a location where they are most useful in absorbing liquid, e.g., blood. The web 92, with or without other components of the end user's product, is then processed into the user's product, such as being included within a feminine hygienic product 100.

Again, with this approach, the end user of the fibers may readily select enhancing agent treated superabsorbent particles to be applied to its product. In addition, the user has flexibility in air laying fibers with enhancing agent treated particles or otherwise combining the enhancing agent treated particles into a finished product with the desired particulates. Accordingly, handling and shipping of the particulate-containing products is avoided by the manufacturer of the pulp sheet, which means that the particles are not subjected to mechanical forces between the location of manufacture of the fibers and the location at which the superabsorbent materials treated with enhancing agents are added.

C. Fiber Characteristics

The present invention includes a method of enhancing the blood absorbent properties of absorbent materials such as superabsorbent particles, and the product, including absorbent end-products, that are produced by such method. In particularly preferred embodiments, the product is a fibrous material such as cellulosic or synthetic fiber combined with superabsorbent material, such as superabsorbent hydrogel polymer particles treated with an enhancing agent, and absorbent products made therefrom. Suitable fibers include bulk fibers in roll form having a basis weight of at least 350 grams per square meter (g/m$^2$) or bale form. The bulk fibers can have a density of at least about 400 kg/m$^3$. Preferred bulk fibers are wood pulp fibers or softwood pulp fibers. The pulp fibers may be chemical or thermomechanical or chemithermomechanical or combinations thereof. The preferred pulp fiber is chemical. Suitable fibers include wood-pulp fibers, which can be obtained from well known chemical processes such as the Kraft and sulfite processes. In these processes, the best starting material is prepared from long fiber coniferous wood species, such as pine, douglas fir, spruce and hemlock. Wood pulp fibers can also be obtained from mechanical processes, such as ground wood, mechanical, thermomechanical, chemimechanical, and chemithermomechanical pulp processes. The fibers are preferably elongated, for example having a length to width ratio of about 100:1 to 5:1.

The fibers of the present invention also include fibers that are pretreated prior to combination with the enhancing agent treated superabsorbent material. This pretreatment may include physical treatment, such as subjecting the fibers to steam or chemical treatment, such as cross-linking the fibers. Although not to be construed as a limitation, examples of pretreating fibers include the application of chelators, deodorants, or hemostatics to the fibers, such as by spraying the fibers with hemostatic chemicals. Specific hemostatic chemicals include, by way of example, cephalin, ethamsylate, hydrastanine hydrochloride, etc. In addition, the fibers may be pretreated with surfactants or other liquids, such as water or solvents, which modify the surface of the fibers. Other pretreatments include exposure to antimicrobials or pigments.

The fibers also may be pretreated in a way which increases their wettability. The fibers also may be pretreated with conventional cross-linking materials and may be twisted or crimped, as desired. Pretreating cellulose fibers with chemicals which result in lignin or cellulose rich fiber surfaces also may be performed in a conventional manner.

Bleaching processes, such as chlorine or ozone/oxygen bleaching may also be used in pretreating the fibers. In addition, the fibers may be pretreated, as by slurrying the fibers in baths containing various solutions. For example, antimicrobial solutions (such as solutions of antimicrobial particles as set forth below), as well as solutions of fragrances and flavors, for release over time during the life of the fibers. Fibers pretreated with other chemicals, such as thermoplastic and thermoset resins also may be used. Combinations of pretreatments also may be employed with the resulting pretreated fibers then being combined with the enhancing agent treated absorbent materials as explained above.

Ground wood fibers, recycled or secondary wood-pulp fibers, and bleached and unbleached wood-pulp fibers can be used. Details of the production of wood pulp fibers are well known to those skilled in the art. These fibers are commercially available from a number of companies, including Weyerhaeuser Company, the assignee of the present invention. The fibers also can be any of a variety of other natural or synthetic fibers. This does not preclude the blending of more than one kind of fiber.

In certain embodiments, in accordance with this aspect of the present invention, as described below in more detail, fibers with hydrogen bond forming functionality may be desirable for bonding treated superabsorbent particles to the fibers. A hydrogen bond is an intermolecular force that occurs between hydrogen atoms that are covalently bonded to small, strongly electronegative elements (such as nitrogen and oxygen) and nonbonding electron pairs on other such electronegative elements. A hydrogen bonding functionality is a functional group that contains an oxygen or nitrogen atom, for example hydroxyls, carboxyls, sulfonic acids, sulfonamides, ethers, esters, epoxides, carbonyls, amines, urethanes and others, that is capable of forming a hydrogen bond. The orbitals of the nonbonding electron pairs on the oxygen or nitrogen overlap with the relatively empty 1s orbital of the hydrogen covalently bonded to another nitrogen or oxygen atom. The 1s orbital of the hydrogen is relatively empty due to the unequal sharing of the electrons in the covalent bond between it and the small electronegative atom (oxygen or nitrogen) to which it is bound.

Specific examples of natural fibers that contain a hydrogen bonding functionality include chopped silk fibers, wood pulp fibers, bagasse, hemp, jute, rice, wheat, bamboo, corn, sisal, cotton, flax, kenaf, peat moss, and mixtures thereof.

Suitable synthetic fibers with hydrogen bonding functionalities include acrylic, polyester, carboxylated polyolefins, rayon and nylon. The hydrogen-bonding functionality is an ester in acrylic fibers and a carboxylic acid in carboxylated polyolefin fibers, an ester in polyester, an amide in nylon, and a hydroxyl in rayon.

For purposes of convenience, and not to be construed as a limitation, the following description proceeds with reference to individual chemical wood-pulp fibers. The fibers are individualized, for example by defiberization in a hammermill. Such individualized fibers are conventionally formed into a mat, and are commercially available, for example as NB 416 fibers from the Weyerhaeuser Company. Another suitable cellulosic mat would include Rayfloc JLD from ITT Rayonier. The cellulose fibers may be in the form of a cellulosic web or loose cellulose fibers.

The particles with enhancing agents of the present invention may be used in combination with fibers that have substantial intrafiber covalent crosslinks (such as HBA available from Weyerhaeuser) or fibers which are substantially free of intrafiber covalent crosslinking. Examples of individualized intrafiber cross-linked fibers are seen in European Patent Applications 440 472 A1 and 427 317 A2, which produce products that those publications describe as being substantially free of interfiber bonds. The fibers of the present invention do not need to be processed as in those European applications to eliminate interfiber bonds. Particles at least partially coated with enhancing agents of the present invention can therefore be used with natural fibers that have substantial interfiber bonding, which are defined as fibers that have not been processed as in European Applications 440 472 A1 and 427 317 A2 to substantially eliminate interfiber bonds. Cellulose fibers that have not been so processed are substantially free of intrafiber bonds.

The fibrous product of the present method (with or without intrafiber crosslinking) may further be densified by external application of pressure. The densified product is compact and easily transported. The resulting fibrous product with incorporated superabsorbent materials has superior blood absorbent properties as compared to untreated products. The inventors have found that the enhancing agents of the present invention produce a product that exhibits enhanced blood absorbent properties, such as free swell blood capacity and after load blood capacity.

D. Superabsorbent Material Characteristics

In accordance with the present invention, superabsorbent materials may be added to the fibers to give the resulting structure desired properties, such as, by way of example only, increased absorbency. The superabsorbent material can be any material, such as particles, granules, or fibers and the like that have the desired property and which is capable of forming hydrogen bonds or coordinate covalent bonds with the enhancing agent. A preferred superabsorbent material includes superabsorbent particles as described below in more detail. In the following description, the superabsorbent material characteristics are described in the context of the exemplary superabsorbent particles.

Hydrogen bonds can be formed, as discussed above, in superabsorbent particles that contain certain functional groups, particularly those having oxygen or nitrogen atoms. Coordinate covalent bonds, in contrast, are formed by donation of an unshared pair of electrons on one atom to an empty orbital of another atom. Coordinate covalent bonds differ from covalent bonds in that covalent bonds are formed by a pair of electrons wherein one of the electrons is donated from each of the atoms that participate in the bond. Particles can form coordinate covalent bonds if they have an empty p or d or f orbital that is capable of accepting a pair of electrons from an oxygen or nitrogen atom in the enhancing agent structure.

A coordinate covalent bond occurs between a donor atom that has an unshared pair of electrons to donate to the bond, and an acceptor atom that has an empty orbital to accept the unshared pair of electrons from the donor. According to the Aufbau and Pauli principles, electrons occupy the lobes of atomic orbitals one at a time with a maximum of two electrons (with opposite spins) per lobe. The most basic orbital is the s orbital, which is available for bonding the elements in the first row of the periodic table. In the second row of the periodic table, electrons fill first the 2s orbital of lithium and beryllium. However, metals in periods less than three do not have sufficient affinity for electrons to participate in coordinate covalent bonding. Beginning with Group IIIB (boron), the three p orbitals may participate in coordinate covalent bonding and the lobes of the p orbitals begin to fill. Boron has one electron in one of the 2p orbitals, thus leaving the other 2p orbitals empty and available for coordinate covalent bonding. An example of a coordinate covalently bonded boron containing particle is boric acid. As shown below, the boron atom of boric acid acts as an acceptor for a lone pair of electrons donated by an oxygen atom of polypropylene glycol (PPG), thereby forming a coordinate covalent bond between a boric acid particle and PPG. This is not representative of typical boron chemistry and is included for illustrative purposes only.

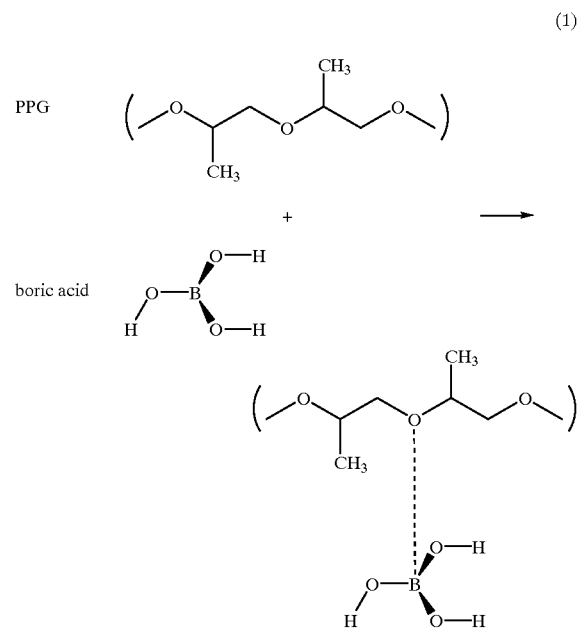

(1)

The next element, carbon, usually hybridizes to have one electron in the 2s orbital and the three remaining electrons are singly placed in the three p orbitals. This leaves no lobes empty for coordinate covalent bonding and electron additions proceeding further across that row of the periodic table also leave no lobes empty. Hence, boron is the only element in the second row of the periodic table that is capable of forming coordinate covalent bonds.

Next the third row begins to fill, and the two 3s electrons fill first in sodium and magnesium, and these metals now have available d orbitals to form coordinate covalent bonds as discussed above. Then aluminum, like boron, places one electron in one of the 3p lobes, and the two other 3p lobes are empty and available for coordinate covalent bonding. The same trends continue across the third row, but the third row elements also have available five 3d lobes so the potential for coordination bonding exists even though 3p orbitals are occupied in the third row. Hence, aluminum, phosphorous, sulfur, and chlorine are capable of accepting a pair of electrons from an electron-pair donor to form a coordinate covalent bond. An example of this is found in the bonding in aluminum hydroxide or phosphorous pentasulfide. An example of a coordinate covalently bonding aluminum compound is aluminum hydroxide, which may participate in a coordinate covalent bond with polypropyleneglycol polymer. In this example, the aluminum atom of aluminum hydroxide acts as an electronic acceptor for an electron pair donated by an oxygen atom of the polypropylene glycol. This is not representative of typical aluminum chemistry and is included for illustrative purposes only.

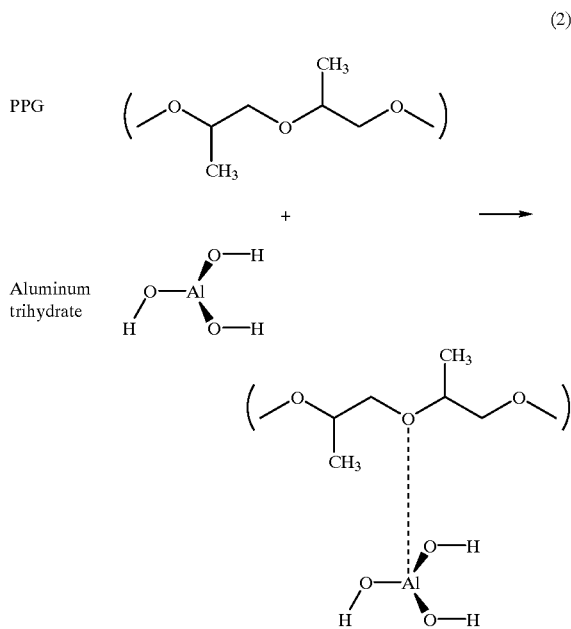

In the next row, the 4s orbital is filled first, then the 3d lobes begin to fill one electron per lobe until all have added a single then a second electron to each lobe until all lobes are filled. However, 4p and 4f orbitals also are available, hence many of the transition elements are capable of forming coordinate covalent bonds.

The elements that have empty orbitals that participate in coordinate covalent bonding include all those except the metals (which excludes hydrogen) in periods one and two, and carbon, nitrogen, oxygen, fluorine, nitrogen, and helium. The alkali metals do not have sufficient affinity for electrons to participate in coordinate covalent bonding.

E. Superabsorbent Particles

In the preferred embodiment the treated superabsorbent material is superabsorbent particles, which comprise polymers that swell on exposure to water and form a hydrated gel (hydrogel) by absorbing large amounts of water. Superabsorbents are defined herein as materials that exhibit the ability to absorb large quantities of liquid, i.e., in excess of 10 to 15 parts of liquid per part thereof. These superabsorbent materials generally fall into three classes, namely starch graft copolymers, cross-linked carboxymethylcellulose derivatives and modified hydrophilic polyacrylates. Examples of such absorbent polymers are hydrolyzed starch-acrylonitrile graft copolymer, a neutralized starch-acrylic acid graft copolymer, a saponified acrylic acid ester-vinyl acetate copolymer, a hydrolyzed acrylonitrile copolymer or acrylamide copolymer, a modified cross-linked polyvinyl alcohol, a neutralized self-crosslinking polyacrylic acid, a cross-linked polyacrylate salt, carboxylated cellulose, and a neutralized cross-linked isobutylenemaleic anhydride copolymer.

Superabsorbent particles are available commercially, for example starch graft polyacrylate hydrogel fines (IM 1000F) from Hoechst-Celanese of Portsmouth, Va., or larger particles such as granules. Other superabsorbent particles are marketed under the trademarks SANWET (supplied by Sanyo Kasei Kogyo Kabushiki Kaisha), SUMIKA GEL (supplied by Sumitomo Kagaku Kabushiki Kaisha and which is emulsion polymerized and spherical as opposed to solution polymerized ground particles), FAVOR (supplied by Stockhausen of Greensboro, N.C.), and NORSOCRYL (supplied by Atochem). The superabsorbent particles come in a variety of sizes and morphologies, for example IM 1000 and IM 1000F. The IM 1000F is finer and will pass through a 200 mesh screen whereas IM 1000 has some particles that will not pass through a 60 mesh screen. Another type of superabsorbent particle is IM 3600 (agglomerated fines). Superabsorbent particulate hydrophilic polymers also are described in detail in U.S. Pat. No. 4,102,340. That patent discloses hydrocolloid absorbent materials such as cross-linked polyacrylamides.

If these particles are combined with the fiber to form an superabsorbent structure, the amount of superabsorbent particles added to the fibers can vary widely, for example, from about 0.05% to 80% of the total weight of the fibrous material and particles. Superabsorbent particles are preferably added in an amount of about 1% to 80%, more preferably about 5% to 70%, and especially preferred 20% to 60% by weight of the fibrous materials and particles.

F. Polymeric Enhancing Agent Characteristics

In accordance with this aspect of the present invention, the blood absorbence properties of the superabsorbent particles may be enhanced by combining the particles with a polymeric enhancing agent. The polymeric enhancing agent is selected from a predetermined group of polymeric enhancing agents. The polymeric enhancing agents comprise polymeric enhancing agent molecules wherein the polymeric enhancing agent molecules have at least one hydrogen bonding functionality or coordinate covalent bond forming functionality. The specific enhancing agents expressly described below are generally organic and have at least one hydrogen bonding functionality. Nonorganic or inorganic enhancing agents may also enhance the blood absorbent properties of superabsorbent materials and would generally form hydrogen bonds or coordinate covalent bonds with the superabsorbent materials.

Preferred enhancing agents may further comprise repeating units, wherein the repeating units have such functionalities on each repeating unit of the polymer, although this is not necessary for adequate enhancing agent functions. In accordance with this aspect of the present invention, the predetermined groups of polymeric enhancing agents include, without limitation, the group of enhancing agents consisting of polyglycols [especially poly (propyleneglycol)], a polycarboxylic acid, a polycarboxylate, a poly(lactone)polyol, such as diols, a polyamide, a polyamine, a polysulfonic acid, a polysulfonate, and combinations thereof. Specific examples of some of these compounds, without limitation, are as follows: polyglycols may include polypropylene glycol (PPG) and polyethylene glycol (PEG); poly(lactone)polyols include poly(caprolactone)diol and poly(caprolactone)triol; polycarboxylic acids include polyacrylic acid (PAA) and polymaleic anhydride; polyamides include polyacrylamide or polypeptides; polyamines include polyethylenimine and polyvinylpyridine; polysulfonic acids or polysulfonates include poly(sodium4-styrenesulfonate) or poly(2-acrylamido-methyl-1-propanesulfonic acid; and copolymers thereof (for example a polypropylene glycol/polyethylene glycol copolymer). The polymeric enhancing agent typically has repeating units. The repeating unit may be the backbone of a compound, such as with a polypeptide, wherein the repeating polyamides occur in the peptide chain. The repeating unit may also refer to units not integral to the polymer backbone, for instance, repeating acrylic acid units. In both cases, the repeating units may be the same or different. In any event, the enhancing agent has a functional group capable of forming a hydrogen bond or a coordinate covalent bond with superabsorbent particles.

As used herein, a polymer is a macromolecule formed by chemical union of 5 or more identical or different combining units (monomers). A polyamine is a polymer that contains amine functional groups and a polyamide is a polymer that contains amide functional groups. Each of the enhancing agents has a hydrogen bonding or a coordinate covalent bonding functionality, and each of the enhancing agents may have such functionalities on each repeating unit (monomer) of the polymer. This repeating functionality may be, without limitation, a hydroxyl, a carboxyl, a carboxylate, a phosphate, a sulfonic acid, a sulfonate, an amide, an ether, an amine or combinations thereof. These enhancing agents are capable of forming hydrogen bonds because they have a functional group that contains an electronegative element, such as oxygen or a nitrogen.

The polyglycol has repeating ether units with hydroxyl groups at the terminal ends of the molecule. The polycarboxylic acid, such as polyacrylic acid, has a repeating carboxyl group in which a hydrogen is bound to an electronegative oxygen, creating a dipole that leaves the hydrogen partially positively charged. The polyamide (such as a polypeptide) or polyamine has a repeating —NR— group in which a hydrogen may be bound to an electronegative nitrogen that also leaves the hydrogen partially positively charged. The hydrogen in both cases can then interact with an electronegative atom, particularly oxygen or nitrogen, on the superabsorbent particle to form a hydrogen bond that adheres the enhancing agent to the particle. The electronegative oxygen or nitrogen of the enhancing agent also can form a hydrogen bond with hydrogen atoms in the superabsorbent particle that have positive dipoles induced by electronegative atoms, such as oxygens or nitrogens, to which the hydrogen is attached. The polyamide also has a carbonyl group with an electronegative oxygen that can interact with hydrogen atoms in the particles.

Although the invention is not limited to polymeric enhancing agents of particular molecular weights, polymeric enhancing agents having a molecular weight less than 1000 grams/mole are preferred because they provide attractive physical properties. Low-molecular weight materials typically are more mobile than are the higher molecular weight materials. Low-molecular weight materials can more easily move into the particle surface. The higher molecular weight materials are less volatile than the low-molecular weight materials. As a result, higher molecular weight polymeric enhancing agents, to a greater extent, remain on the surface of the particles. In some particular embodiments, polymers with molecular weights between 4000 and 8000 grams/mole have been used. Polymers with molecular weights above 8000 may be used, but such exceedingly high molecular weight polymers may decrease product efficiency.

In accordance with this aspect of the present invention wherein a polymeric enhancing agent is applied to the superabsorbent particles, polyethylene glycol is a particularly preferred polymeric enhancing agent when the superabsorbent particle is IM 3900 as described above. When 0.5% by weight polyethylene glycol based on the combined weight of the superabsorbent particles and the enhancing agent is combined with 99.5% by weight IM 3900 superabsorbent particles, the increase in the free swell absorbent capacity and after load absorbent capacity is described below in the examples.

G. Non-Polymeric Enhancing Agent Characteristics

The blood absorbent properties of superabsorbent particles may be enhanced by combining the particles with a non-polymeric organic enhancing agent selected from a predetermined group of enhancing agents that each have a volatility less than water. The vapor pressure of the enhancing agent may, for example, be less than 10 mm Hg at 25° C., and more preferably less than 1 mm Hg at 25° C. The non-polymeric enhancing agents useful in this aspect of the present invention comprise non-polymeric enhancing agent molecules wherein the non-polymeric enhancing agent molecules have at least one functional group that forms hydrogen bonds or coordinate covalent bonds with the superabsorbent particles. The non-polymeric enhancing agents that are expressly described below are organic and generally include at least one hydrogen bond forming functionality. Other nonorganic or inorganic non-polymeric enhancing agents may also enhance the blood absorbent properties of the superabsorbent particles in accordance with the present invention and generally form hydrogen bonds or coordinate covalent bonds with the superabsorbent particles. In accordance with the present invention, the predetermined group of non-polymeric enhancing agents may include a functional group selected from, without limitation, the group consisting of a carboxyl, a carboxylate, a carbonyl, a sulfonic acid, a sulfonamide, a sulfonate, a phosphate, a phosphoric acid, a phosphoramide, a hydroxyl, an amide, an amine, and combinations thereof (such as an amino acid or a hydroxy acid) wherein each enhancing agent preferably includes at least two such functionalities, and the two functionalities are the same or different. As used herein, the term "non-polymeric" refers to a monomer, dimer, trimer, tetramer, and oligomers, although some particular non-polymeric enhancing agents are monomeric and dimeric, preferably monomeric.

Suitable non-polymeric organic enhancing agents are capable of forming five or six membered rings with a functional group on or near the surface of the superabsorbent particle. An example of such a enhancing agent is an amine or amino acid (for example, a primary amine or an amino acid such as glycine) which forms six-membered rings by forming hydrogen bonds:

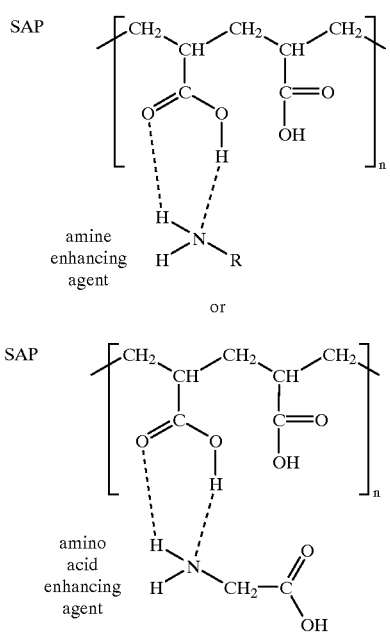

(3)

amine enhancing agent or (3 continued)

amino acid enhancing agent

A six-membered ring also is formed by the hydroxyl groups of carboxylic acids, alcohols, and amino acids, for example:

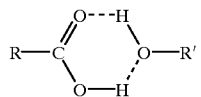

(4)

A five membered ring can be formed by the enhancing agent and the functionality on or near the surface of the particle, for example:

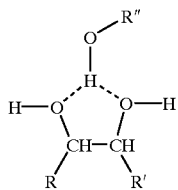

(5)

wherein the particle is a water-insoluble superabsorbent particle and the enhancing agent is an alcohol, such as a polyol with hydroxyl groups on adjacent carbons, for example 2,3-butanediol.

Other alcohols that do not form a five-membered ring also can be used, for example alcohols that do not have hydroxyl groups on adjacent carbons. Examples of suitable alcohols include primary, secondary or tertiary alcohols.

Amino alcohol enhancing agents are alcohols that contain an amine group (—NR$_2$), and include enhancing agents such as ethanolamine (2-aminoethanol), and diglycolamine (2-(2-aminoethoxy)ethanol). Non-polymeric polycarboxylic acids contain more than one carboxylic acid functional group, and include such enhancing agents as citric acid, propane tricarboxylic acid, maleic acid, butanetetracarboxylic acid, cyclopentanetetracarboxylic acid, benzene tetracarboxylic acid and tartaric acid. A polyol is an alcohol that contains a plurality of hydroxyl groups, and includes diols such as the glycols (dihydric alcohols) ethylene glycol, propylene glycol and trimethylene glycol; triols such as glycerin (1,2,3-propanetriol). Esters of hydroxyl containing enhancing agents and polyhydroxy or polycarboxylic acid compounds such as tartaric acid or ascorbic acid (vitamin C) may also be used, with mono- and di-esters of glycerin as examples:

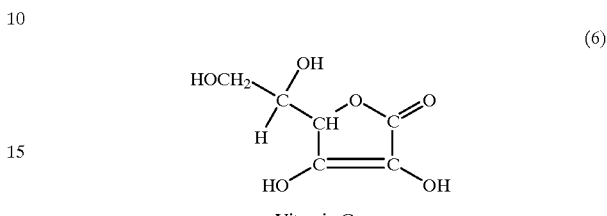

Vitamin C
(ascorbic acid)

Hydroxy acid enhancing agents are acids that contain a hydroxyl group, and include hydroxyacetic acid (CH$_2$OHCOOH) and lactic, tartaric, ascorbic, citric, and salicylic acid. Amino acid enhancing agents include any amino acid, such as glycine, alanine, valine, serine, threonine, cysteine, glutamic acid, lysine, or β-alanine.

Sulfonic acid enhancing agents and sulfonates are compounds that contain a sulfonic acid group (—SO$_3$H) or a sulfonate (—SO$_3^-$) Amino-sulfonic acids also can be used. One example of an amino-sulfonic acid enhancing agent suitable for the present invention is taurine, which is 2-aminoethanesulfonic acid.

Non-polymeric polyamide enhancing agents are small molecules (for example, monomers or dimers) that have more than one amide group, such as oxamide, urea and biuret. Similarly, a non-polymeric polyamine enhancing agent is a non-polymeric molecule that has more than one amine group, such as ethylene diamine, EDTA or the amino acids asparagine and glutamine.

Although other non-polymeric organic enhancing agents are suitable in accordance with the discussion above, the non-polymeric organic enhancing agent is preferably selected from the group consisting of glycerin, sorbitol, lactic acid, ascorbic acid, urea, glycine, ammonium citrate, taurine, dipropylene glycol, aminosalicylic acid, and combinations thereof. The non-polymeric enhancing agent also is most preferably selected from the group consisting of glycine, sorbitol, lactic acid, a polyglycerin oligomer, and combinations thereof. As used herein, an oligomer refers to a condensation product of polyols, wherein the condensation product contains less than ten monomer units. A polyglycerin oligomer as referred to herein means a condensation product of two or more glycerin molecules. A propylene glycol oligomer as referred to herein means a condensation product of two or more propylene glycol molecules. The non-polymeric enhancing agents also preferably include functionalities selected, without limitation, from the group consisting of a carboxyl, a carboxylate, a carbonyl, a sulfonic acid, a sulfoamide, a sulfonate, a phosphate, a phosphoric acid, a phosphoramide, a hydroxyl, an amine, an amide, and combinations thereof (such as amino acids and hydroxy acids). The non-polymeric enhancing agents may have two functionalities from such group, and the groups may be the same or different.

Each of the non-polymeric enhancing agents disclosed above is capable of forming hydrogen bonds because it has a functional group that contains electronegative atoms, particularly oxygens or nitrogens, or has electronegative groups, particularly groups containing oxygens or nitrogens, that also may include a hydrogen. An amino alcohol, amino acid, carboxylic acid, alcohol and hydroxy acid all have a hydroxyl group in which a hydrogen is bound to an electronegative oxygen, creating a dipole that leaves the hydrogen partially positively charged. The amino alcohol, amino acid, amide and amine all have an —NR— group in which a hydrogen may be bound to an electronegative nitrogen that also leaves the hydrogen partially positively charged. The partially positively charged hydrogen in both cases then can interact with an electronegative element, such as oxygen or nitrogen, on the superabsorbent particle to help adhere the enhancing agent to the particle. The polycarboxylic acid, hydroxy acid, amino acid and amide also have a carboxyl group with an electronegative oxygen that can interact with hydrogen atoms in the particles, or in intermediate molecules between the enhancing agent and particles. Similarly, electronegative atoms (such as oxygen or nitrogen) on the particle can interact with hydrogen atoms on the enhancing agent that have positive dipoles, and partially positive hydrogen atoms on the particle can interact with electronegative atoms on the enhancing agent.

Alternatively, an atom on the superabsorbent may have an unbound pair of electrons, such as an unshared pair of electrons from an oxygen or nitrogen atom, that can be donated to an empty orbital of an acceptor atom in the enhancing agent to form a coordinate covalent bond. The free pair of electrons on the oxygen or nitrogen can be donated to the empty p, d or f orbital of an enhancing agent to form a coordinate covalent bond that adheres the particle to the enhancing agent. Cellulose fibers themselves do not normally contain functional groups that can act as electron acceptors in the formation of coordinate covalent bonds with the enhancing agents, but they also contain functionality that may be electron donors in the formation of a coordinate covalent bond. Cellulosic and synthetic fibers, for example, contain hydroxyl, carboxyl and ester groups that will hydrogen bond with the hydroxyl, carboxylic acid, amide, amine, or other groups of the enhancing agent. Non-cellulosic or non-synthetic fibers that have these functionalities also can be used, for example silk or wool, which have an amide linkage. When it is desired to bond the enhanced superabsorbent particles to the fiber, the enhancing agent may adhere to the superabsorbent particle and a fiber with a coordinate covalent bond or a hydrogen bond.

As described above, non-polymeric enhancing agents have functional groups that may be selected independently or in combination, without limitation, from the group consisting of a carboxyl, a carboxylate, a carbonyl, a hydroxyl, a sulfonic acid, a sulfonate, a phosphoric acid, a phosphate, a phosphoramide, a sulfonamide, an amide, an amine, and combinations thereof. These functional groups might be provided by the following exemplary chemical compounds: a carboxyl group could be provided by carboxylic acids, such as ascorbic acid; a carboxylate, which is an ionized carboxylic acid, could be provided by a material such as potassium citrate; a carbonyl group can be provided by an aldehyde or ketone; a hydroxyl can be provided by an alcohol or polyol, such as glycerol, or a mono- or diglyceride, which are esters of glycerol; an amide, such as a urea; and an amine, which may be provided by an alkyl amine, such as ethanolamine, wherein the enhancing agent has two of these functional groups, and each of the functional groups can be the same (for example, a polyol, polyaldehyde, polycarboxylic acid, polyamine or polyamide) or different (for example, an amino alcohol, hydroxy acid, hydroxyamide, carboxyamide, or amino acid) Functional groups also may be selected independently or in combination, without limitation, from the group consisting of carboxyl, an alcohol, an amide and an amine. An aldehyde may optionally be a member of each of these groups, particularly if it is oxidized to a carboxylic acid.

Combinations of polymeric and non-polymeric enhancing agents may also be used, with or without other enhancing agents, providing that they are non-reactive. That is, providing that the enhancing agents do not react in a manner which prevents the enhancing agents from enhancing the blood absorbence properties of the superabsorbent materials in accordance with the present invention.

The enhancement of the blood absorbence properties of superabsorbent particles IM 3900, IM 1000, FAVOR 800, J 44, and Aridal 1440 when treated with varying amounts of non-polymeric enhancing agents are described in the examples that follow.

H. Process Advantages

The enhancing agents of the present invention also provide numerous process advantages. For example, a liquid enhancing agent (which would include a solution of a solid or liquid enhancing agent, or a enhancing agent that has a melting point below room temperature) can be applied to particles and the enhancing agent allowed to air dry, for example until the particles reach an equilibrium moisture content with the moisture in the ambient air. The particles with enhancing agent then may be added to a fiber mat. Alternatively, the particles and enhancing agent may be added to a mat prior to or simultaneously with the coating of the particles by the enhancing agent.

The enhancing agents may be liquids at room temperature (such as glycerin), or liquid solutions of enhancing agents that are solids at room temperature (for example, an aqueous solution of glycine), or liquid hot melts of solid enhancing agents. In a liquid form, the enhancing agents can be applied to and allowed to at least partially coat or embed themselves in the superabsorbent particles in the absence of serous bodily fluids. By applying the enhancing agents directly to the superabsorbent particles, one can readily control and monitor the amount of enhancing agent applied to the superabsorbent material.

The polymeric enhancing agent suitably is present in an amount of at least about 0.01%, and no more than about 10%, by weight of the particles ("percent by weight"). In preferred embodiments, the polymeric enhancing agent is present in an amount of about 0.01% to about 8%, more preferably about 0.01% to about 3%, and even more preferably about 0.01% to about 1% by weight of the particles. When the polymeric enhancing agent is present in the above amounts in accordance with this aspect of the present invention, the free swell blood absorbent capacity of the treated superabsorbent particles is preferably at least about 1.15 times, and more preferably at least 1.5 times the free swell blood absorbent capacity of the untreated superabsorbent particles. In another preferred aspect, when the polymeric enhancing agent is used in the above amounts, the after load blood absorbent capacity of the treated superabsorbent particles is preferably at least about 1.15 times, and more preferably at least about 1.5 times the after load blood absorbent capacity of the untreated particles. Specific embodiments of this aspect of the present invention are set forth in the examples.

The nonpolymeric enhancing agent suitable is present in an amount of at least about 0.01% and no more than about 10%, by weight of the superabsorbent particles. In preferred embodiments, the nonpolymeric enhancing agent is present in an amount of about 0.01% to about 8%, more preferably about 0.01% to about 3%, and even more preferably about 0.01% to about 1% by weight of the superabsorbent particles. In particularly preferred embodiments, wherein the nonpolymeric enhancing agent is glycerin, the amount used is about 0.05% to about 0.1% by weight of the superabsorbent particles. When the nonpolymeric enhancing agent is used in the above amounts, the free swell blood absorbent capacity of the treated superabsorbent particles is preferably at least about 1.2, and more preferably at least double the free swell blood absorbent capacity of the untreated superabsorbent particles. In another preferred aspect, when the nonpolymeric enhancing agent is used in the above amounts, the after load blood absorbent capacity of the treated superabsorbent particles is preferably at least about 1.2 times, and more preferably at least double the after load blood absorbent capacity of the untreated superabsorbent particles. Using excessive amounts of enhancing agent can introduce unnecessary expense into the process. High percentages of enhancing agent can also cause processing problems because the enhancing agent material transfers to equipment surfaces. Therefore, it is often preferred to use no more enhancing agent than is required to enhance the blood absorbent properties of the superabsorbent particles.

Thermoplastic enhancing agents also may be used to help enhance other properties of the superabsorbent particles or absorbent articles made therefrom. The enhancing agents that have the hydrogen bonding or coordinate covalent bonding functionalities may be thermoplastic. The polymeric enhancing agents and some non-polymeric enhancing agents of the present invention have the advantage of being thermoplastic or meltable solids.

In accordance with this aspect of the present invention as briefly described above, the enhancing agents may be applied to superabsorbent particles before, or simultaneously with, addition of the superabsorbent particles to the fibers. A preferred approach is to simply spray, as by a mist or fog, the enhancing agent onto the particles as the particles are delivered to the fibers. Simultaneous addition can be accomplished by two separate streams of particles and enhancing agent that are simultaneously directed at a fibrous substrate, or alternatively merged immediately or some time prior to impacting against the substrate. Some of the enhancing agent may reach the fibers without impacting a particle, but the bulk of the particles will be at least partially coated with the enhancing agent or have the enhancing agent at least partially embedded in its surface.

II. Enhancing Agents on Fibrous Material

In a second aspect of the present invention, enhancing agents described below in more detail may be used to enhance the blood absorbence properties of a superabsorbent material, such as superabsorbent particles. In accordance with this aspect of the present invention, the enhanced blood absorbence properties are achieved by providing the enhancing agent on a fibrous material as opposed to the superabsorbent material as described above with respect to Section I. The coated fibrous material can be combined with the superabsorbent material to form an absorbent composition. The following description of a preferred embodiment of this aspect of the present invention refers to superabsorbent particles and cellulose fibers. It should be understood that other types of fibers, both natural and synthetic as described below in more detail, can also be used as the fibrous material. In addition to superabsorbent particles, superabsorbent materials in other forms, such as fibers, are equally useful in accordance with the present invention.

A. Processing of Fibers

A wet laid sheet manufacturing line for producing one embodiment of an absorbent composition in accordance with this aspect of the present invention has been described above with respect to FIG. 1.

An enhancing agent of the type explained in detail below is applied to the pulp sheet from one or more enhancing agent applying devices, one of which is indicated at 50 in FIG. 1. Any enhancing agent applying device may be used, such as sprayers, roll coaters, immersion applicators or the like. Sprayers are typically easier to utilize and incorporate into a pulp sheet manufacturing line. As indicated by the arrows 52, 54 and 56, the enhancing agent may be applied at various locations or at multiple locations on the pulp sheet manufacturing line, such as ahead of the drying stage 30 (indicated by line 52), intermediate the drying stage 30 (as indicated by line 54), or downstream from the drying stage 30 (as indicated by the line 56). Water-based enhancing agents, such as non-polymeric urea, are typically applied at a location where sufficient drying can still take place in the drying stage to produce a dried enhancing agent containing fiber sheet with no more than the maximum desired moisture content. Consequently, to take advantage of the drying stage 30, water-based enhancing agents are typically applied at locations 52 or 54. At location 52, the water remaining in the sheet or mat 20 at this stage tends to interfere with the penetration of the enhancing agent into the sheet. Consequently, application of the enhancing agent after some drying has taken place, for example at location 54, is preferable. If water-based enhancing agents are applied at location 56 in an amount which would cause the moisture content of the sheet to exceed the desired maximum level, an additional drying stage (not shown) may be included in the pulp manufacturing line to bring the moisture content down to the desired level.

A non-aqueous based enhancing agent, such as glycerin, is most preferably added downstream from the drying stage at location 56 or during the drying stage as indicated by location 54. However, liquid non-aqueous enhancing agent may also be added at a location, such as location 52, upstream of the drying stage. At this latter location, the water in the wet web at this point may tend to attract these enhancing agents into the mat or sheet as the enhancing agents tend to be hydroscopic. Since non-aqueous enhancing agents typically do not enhance the degradation of the product due to the addition of moisture to the sheet, they can be applied downstream from the drying stage without bringing the moisture content of the sheet above the desired maximum level.

The superabsorbent materials, selected as explained below, may be added to the sheet on the pulp manufacturing line, such as indicated by the particulate applicator 60, which may comprise a bulk or volumetric metering device. These particles may be sprinkled, poured or otherwise added to the sheet.

As described above, during transportation of rolls or bales of these fibers it is possible for particles to become dislodged by mechanical impact during transport. In addition, this approach interferes with the customization of the fiber application at a user's location. For example, a user may want the capability of selecting particular types or brands of superabsorbent particles for use with the fibers in the user's products, without having this selection made by a pulp sheet manufacturer who incorporates the particles into the pulp sheet during its manufacture. Also, superabsorbent particles are susceptible to absorbing moisture from the atmosphere during shipment. Therefore, it is also advantageous to provide a fibrous product in which the end user of the product may incorporate the desired superabsorbent particles at the time the fibers are converted into products.

Therefore, in keeping with this latter preferred approach, as illustrated in FIG. 2, the respective rolls 40 or bales 44 of enhancing agent containing fibers can be produced, without particles, and then transported to a remote location for use by a user, as described above with reference to the enhancing agent treated particles.

With this approach, the end user of the fibers may readily select superabsorbent particles to be combined with the treated fibers. In addition, the user has flexibility in air laying or otherwise combining the enhancing agent containing fibers into a finished product with the desired superabsorbent. When the enhancing agents are water-soluble, the enhancing agent containing fibers are preferably not wet laid because wet laying would remove at least some of the enhancing agent. In the foregoing approach, not only is handling and shipping of the superabsorbent containing products avoided by the manufacturer of the pulp sheet, the particles are not subjected to mechanical forces between the location of manufacture of the fibers and the location at which the particulate materials are added.

B. Fiber Characteristics

The fibrous material, which may be treated with enhancing agent in accordance with this aspect of the present invention, has been generally described above in Section IB.

C. Superabsorbent Material and Particles Characteristics

In accordance with this aspect of the present invention, the fibrous material treated with the enhancing agent is combined with a superabsorbent material, that may be in the form of particles or fibers to enhance the blood absorbence properties of the superabsorbent material and provide an absorbent composition that has enhanced blood absorbent properties. The superabsorbent materials that are useful in this aspect of the present invention have been generally described above in Sections IC and ID. In accordance with this aspect of the present invention, wherein the enhancing agent is applied to the fibrous material, it is preferred that the superabsorbent materials include functionality capable of forming hydrogen bonds or coordinate covalent bonds with the enhancing agent.

D. Polymeric Enhancing Agent Characteristics

The enhancing agents useful in accordance with this aspect of the present invention include a polymeric enhancing agent, which may be water soluble, selected from a predetermined group of polymeric enhancing agents. The polymeric enhancing agents have been generally described above in Section IF. The polymeric enhancing agents comprise enhancing agent molecules, wherein the enhancing agent molecules have at least one hydrogen bonding or at least one coordinate covalent bonding functionality for forming a hydrogen or coordinate covalent bond with the superabsorbent material. The polymeric enhancing agents specifically described below are generally organic in nature and include at least one hydrogen bonding functionality for forming a hydrogen bond with the superabsorbent material. Other nonorganic or inorganic polymeric enhancing agents may be applied to the fibrous material to enhance the blood absorbent properties of a superabsorbent material to be combined with the treated fibrous material. Such inorganic polymeric enhancing agents will generally form at least one hydrogen or coordinate covalent bond with a superabsorbent material. In accordance with this aspect of the present invention, the enhancing agent in addition to having functionality capable of forming hydrogen bonds or coordinate covalent bonds with the superabsorbent material, can also include functionality that allows the enhancing agent to bond to the fibrous material. Such bonding to the fibrous material would be particularly preferred where one desires to bind the superabsorbent particles thereto and the superabsorbent material.

When it is desirable to bond the enhancing agent to the fibrous material, the polymeric enhancing agent has functionality to form a hydrogen bond or a coordinate covalent bond with the fibers. For example, the oxygen or nitrogen on the enhancing agent has an unbound pair of electrons that can be shared with a partially positive hydrogen in the particle or a fiber. Coordinate covalent bond formation has been described above in more detail in Section IC.

The fibers themselves may contain functional groups that can form hydrogen bonds with the enhancing agent, and allow the enhancing agent to adhere to the fiber. Cellulosic and synthetic fibers, for example, may contain hydroxyl, carboxyl, carbonyl, amine, amide, ether and ester groups that will hydrogen bond with the hydroxyl, carboxylic acid, amide or amine groups of the enhancing agent.

In some embodiments, the polymeric enhancing agent is bound to both the fibers and the particle by hydrogen bonds. In a polypropylene glycol enhancing agent, for example, the hydroxyl and ether groups on the glycol enhancing agent participate in hydrogen-bonding interactions with the hydroxyl groups on the cellulose fibers and the carboxyl groups on the polyacrylate hydrogel, as shown below:

(A)

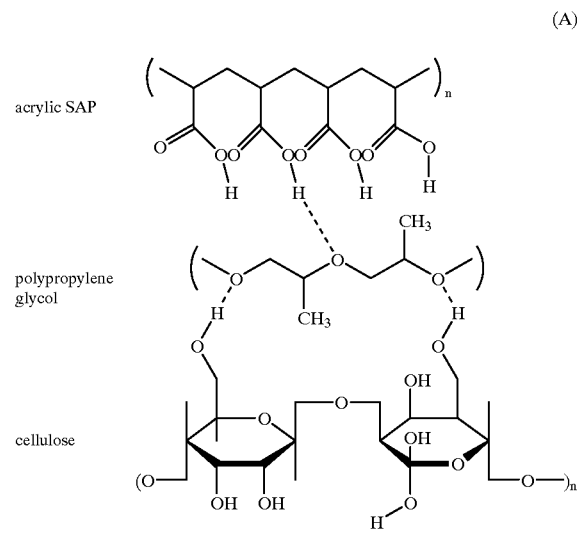

Although this aspect of the invention is not limited to polymeric enhancing agents of particular molecular weights, polymeric enhancing agents having a molecular weight less than 1000 grams/mole are preferred because they provide attractive physical properties. Polymeric enhancing agents with molecular weights less than 4000 grams/mole are especially preferred because they have sufficiently low volatility and are not likely to evaporate from the fibers. Low-molecular weight materials typically are more mobile than are the higher-molecular weight materials. Low-molecular weight materials can more easily move to the fiber or the particle surface. The higher molecular weight materials are less volatile than the low-molecular weight materials. As a result, higher molecular weight polymeric enhancing agents, to a greater extent, remain on the surface of the fibers. In some particular embodiments, polymers with molecular weights between 4000 and 8000 grams/mole have been used. Polymers with molecular weights above 8000 may be used, but such exceedingly high molecular weight polymers may decrease product efficiency.

E. Non-Polymeric Enhancing Agent Characteristics

In accordance with this aspect of the present invention, the blood absorbency properties of the absorbent composition of superabsorbent material and fibrous material may be enhanced by a non-polymeric organic enhancing agent selected from a predetermined group of enhancing agents that each have a volatility less than water. Non-polymeric enhancing agents useful in accordance with this aspect of the present invention have been generally described above in Section IG. The vapor pressure of the non-polymeric enhancing agent may, for example, be less than 10 mm Hg at 25° C., and more preferably less than 1 mm Hg at 25° C. The non-polymeric enhancing agents comprise non-polymeric enhancing agent molecules wherein the molecules have at least one functional group that forms hydrogen bonds with the superabsorbent material. In accordance with this aspect of the present invention, as with the polymeric enhancing agents, the non-polymeric enhancing agents expressly described below are organic and generally form hydrogen bonds with the superabsorbent material. Nonorganic or inorganic non-polymeric enhancing agents applied to a fibrous material to be combined with a superabsorbent material may also enhance the blood absorbence properties of the superabsorbent material. Such inorganic enhancing agents will generally form a hydrogen bond or coordinate covalent bond with the superabsorbent material.

As with the polymeric enhancing agents described in the previous section, the non-polymeric enhancing agents may or may not form bonds with the fibrous material. If such bonds are formed, they are generally of the hydrogen type or coordinate covalent type. Accordingly, since it is not required that enhancing agent bond to the fibrous material, fibrous materials that do not include hydrogen bonding or coordinate covalent bond forming functionality are also useful in accordance with the present invention. If the enhancing agent is to be bound to the fibrous, the non-polymeric enhancing agent preferably has at least one functional group that forms hydrogen bonds or coordinate covalent bonds with the fibers. In accordance with this aspect of the present invention, the predetermined group of non-polymeric enhancing agents may include, without limitation, a functional group selected from the group consisting of a carboxyl, a carboxylate, a carbonyl, a sulfonic acid, a sulfonate, a phosphate, a phosphoric acid, a hydroxyl, an amide, an amine, and combinations thereof (such as an amino acid or hydroxy acid) wherein each enhancing agent preferably includes at least one such functionality.

As used herein, the term "non-polymeric" refers to a monomer, dimer, trimer, tetramer, and oligomers, although some particular non-polymeric enhancing agents are monomeric and dimeric, preferably monomeric.

Suitable non-polymeric organic enhancing agents capable of forming five or six membered rings with a functional group on the surface of the superabsorbent material, have been described above in Section IG. Alcohols that do not form a five-membered ring, amino alcohol enhancing agents, non-polymeric polycarboxylate acid enhancing agents, polyol enhancing agents, esters of hydroxyl containing enhancing agents, hydroxy acid enhancing agents, amino acid enhancing agents, sulfonic acid enhancing agents, amino sulfonic acid enhancing agents, non-polymeric polyamide enhancing agents, and non-polymeric polyamine enhancing agents have been described above in Section IG.

Although other non-polymeric organic enhancing agents are suitable in accordance with the discussion above, the non-polymeric organic enhancing agent is preferably selected from the group consisting of glycerin, sorbitol, lactic acid, ascorbic acid, urea, glycine, ammonium citrate, taurine, dipropylene glycol, aminosalicylic acid, and combinations thereof. The non-polymeric enhancing agent also is most preferably selected from the group consisting of glycerin, sorbitol, lactic acid, and combinations thereof. The non-polymeric enhancing agents also preferably include functionalities selected from the group, without limitation, consisting of a carboxyl, a carboxylate, a carbonyl, a sulfonic acid, a sulfonate, a phosphate, a phosphoric acid, a hydroxyl, an amine, an amide, and combinations thereof (such as an amino acid or hydroxy acid). The non-polymeric enhancing agents preferably have at least one functionality from such group.

Each of the non-polymeric enhancing agents disclosed above is capable of forming hydrogen bonds because it has a functional group that contains electronegative atoms, particularly oxygens or nitrogens, or has electronegative groups, particularly groups containing oxygens or nitrogens, and that also include a hydrogen. The amino alcohol, amino acid, carboxylic acid, alcohol and hydroxy acid all have a hydroxyl group in which a hydrogen is bound to an electronegative oxygen, creating a dipole that leaves the hydrogen partially positively charged. The amino alcohol, amino acid, amide and amine all have an -NR- group in which a hydrogen may be bound to an electronegative nitrogen that also leaves the hydrogen partially positively charged. The partially positively charged hydrogen in both cases then can interact with an electronegative element, such as oxygen or nitrogen, preferably on the superabsorbent material and possibly on the fiber. The polycarboxylic acid, hydroxy acid, amino acid and amide also have a carboxyl group with an electronegative oxygen that can interact with hydrogen atoms preferably on the superabsorbent material and possibly on the fibers, or in intermediate molecules between the enhancing agent and substrate. Similarly, electronegative atoms (such as oxygen or nitrogen) on the superabsorbent material or fiber can interact with hydrogen atoms on the enhancing agent that have positive dipoles, and partially positive hydrogen atoms on the superabsorbent material or fiber can interact with electronegative atoms on the enhancing agent.

Several proposed hydrogen bonding interactions of two of the enhancing agents (glycine and 1,3-propanediol) with cellulose are shown below:

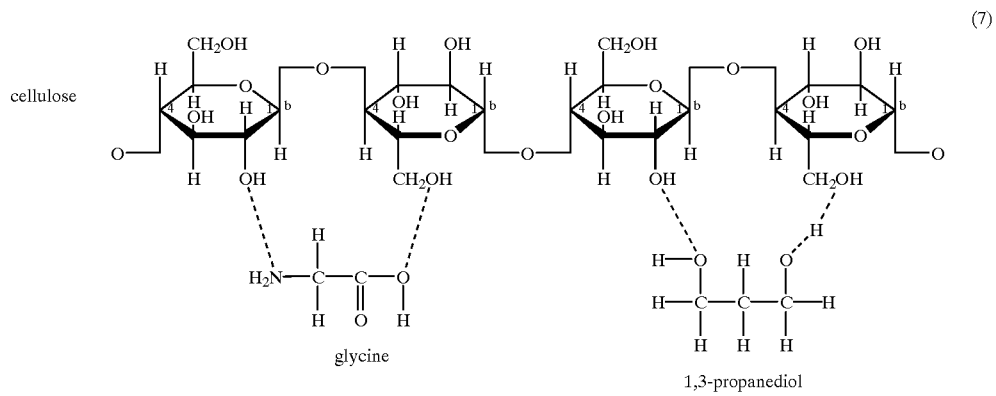

(7)

The hydrogen bonding interactions are shown as dotted lines. One such interaction is shown between the nitrogen of glycine and a hydrogen of an —OH on cellulose. A hydrogen bond with glycine is also shown between an oxygen of the —OH on glycine and the hydroxy hydrogen of an alcohol sidechain on cellulose. Hydrogen bonding interactions of the 1,3-propanediol are shown in dotted lines between an oxygen on an —OH group of the enhancing agent and a hydrogen of an —OH group on the cellulose molecule. Another hydrogen bond is also shown between a hydrogen on an —OH group of the glycol enhancing agent and an oxygen in an alcohol sidechain of the cellulose.

It also is possible for water or other hydrogen bonding molecules to be interposed between the fiber and enhancing agent, such that the fiber and enhancing agent are both hydrogen bonded to the water molecule.

Alternatively, in an embodiment wherein the enhancing agent is bound to the fibers, an atom on the non-polymeric enhancing agent may have an unbound pair of electrons, such as a lone pair of electrons from an oxygen or nitrogen atom, that can be donated to an empty orbital of an acceptor atom in the particle to form a coordinate covalent bond. The free pair of electrons on the oxygen or nitrogen can be donated to the empty p, d or f orbital of a particle to form a coordinate covalent bond that adheres the particle to the non-polymeric enhancing agent. Coordinate covalent bonding has been discussed above in more detail. The fibers themselves do not normally contain functional groups that can act as electron acceptors in the formation of coordinate covalent bonds with the non-polymeric enhancing agents, but hydrogen bonding interactions allow the enhancing agent to adhere to the fiber. Cellulosic and synthetic fibers, for example, contain hydroxyl, carboxyl and ester groups that will hydrogen bond with the hydroxyl, carboxylic acid, amide, amine or other groups of the non-polymeric enhancing agent. Non-cellulosic or non-synthetic fibers that have these functionalities also can be used, for example silk, which has an amide linkage.

In some embodiments, the non-polymeric enhancing agent can bind to both the fibers and the particle by hydrogen bonds. The hydroxyl groups on a polyol enhancing agent participate in hydrogen-bonding interactions with the hydroxyl groups on cellulose fibers and the carboxyl groups on a polyacrylate hydrogel.

A structural drawing is shown below in which citric acid, vitamin C and urea bond to both water-insoluble superabsorbent particles and to cellulose with hydrogen bonds. Some of the possible hydrogen bonding interactions are shown as dashed lines. It is possible that other molecules (such as water molecules) also may participate in some of these bonds, for example, as an intermediary between the enhancing agent and particle or fiber.

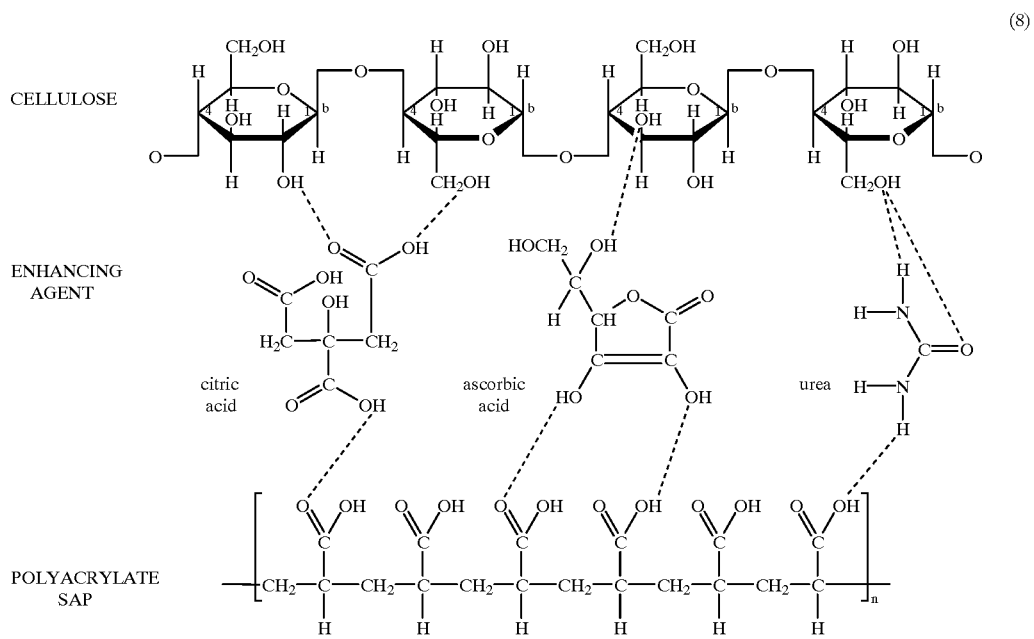

(8)

Non-polymeric enhancing agents have functional groups that may be selected, without limitation, independently or in combination from the group consisting of a carboxyl, a carboxylate, a carbonyl, a hydroxyl, a sulfonic acid, a sulfonate, a phosphoric acid, a phosphate, an amide, an amine, and combinations thereof. These functional groups might be provided by the following exemplary chemical compounds: a carboxyl group could be provided by carboxylic acids, such as ascorbic acid; a carboxylate, which is an ionized carboxylic acid, could be provided by a material such as ascorbate; a carbonyl group can be provided by an aldehyde, such as ketone; a hydroxyl, such as an alcohol or a polyol, such as glycerol, or a mono- or diglyceride, which are esters of glycerol; an amide, such as a peptide; and an amine, which may be provided by an alkyl amine, such as ethylenimine wherein the enhancing agent preferably has at least one of these functional groups. Functional groups also may be selected independently or in combination from the group consisting of carboxyl, an alcohol, an amide and an amine. An aldehyde may optionally be a member of each of these groups, particularly if it is oxidized to a carboxylic acid.

Combinations of the polymeric and non-polymeric enhancing agents, may be used, providing that they are non-reactive. That is, providing that the enhancing agents do not react in a manner which prevents them from enhancing the blood absorbence properties of the absorbent composition, in accordance with this aspect of the present invention.

When the enhancing agent is capable of bonding to the fibrous material, although such bonding is permissible, it should not inhibit the enhancing agent from enhancing the blood absorbence properties of the superabsorbent material. Accordingly, it is preferred that when the enhancing agent is capable of bonding to the fibrous material, that an amount of the enhancing agent effective to enhance the blood absorbence properties of the superabsorbent material be available to bond to the superabsorbent materials as described above.

F. Process Advantages

The enhancing agents of the present invention also provide numerous process advantages. For example, a liquid enhancing agent (which would include a solution of a solid or liquid enhancing agent, or a enhancing agent that has a melting point or softening point below room temperature) can be applied to a cellulose mat in and the enhancing agent allowed to dry, for example until the fiber product reaches an equilibrium moisture content with the moisture in the ambient air. The coated fibers may then be combined with superabsorbent materials such as particles or fibers. Some of the enhancing agents (especially the liquid enhancing agents) diffuse throughout the fibers to reach an equilibrium distribution of the enhancing agent. Alternatively, the particles may be added to the mat prior to or simultaneously with the coating of the fibers with the enhancing agent.

The enhancing agents may be liquids at room temperature (such as glycerin), or liquid solutions of enhancing agents that are solids at room temperature (for example, an aqueous solution of glycine), or liquid hot melts of solid enhancing agents. Solid enhancing agents can be applied to the fibers as a supersaturated solution or the solid enhancing agent may be heated above its melting point and applied to the fibers. By applying the enhancing agent to the fibrous material, uniform dispersion of the enhancing agent throughout the matrix of the absorbent composition is readily achievable.

The fiber coating of the present invention can occur across a broad range of pH without requiring a catalyst. A suitable pH range without a catalyst is 1–14, but preferred ranges are 5–8 or 6–8 because such neutral pH ranges will produce fibrous products (such as cellulose products) that are less prone to damage by acid hydrolysis.

The moisture content of the fibers during the coating step is 0.5–50%, suitably 5–40%, or preferably 5–20% water by weight of the fibers, enhancing agent and particles. Particles may be added to the fibers with the particles distributed throughout a fibrous product without being confined to a surface of the product. The particles can be distributed throughout the depth of a fiber product such as a mat or web.

The enhancing agent suitably is present on the treated fibers in an amount of about 2% to 30% of the total weight of the fibers and enhancing agent, more preferably, about 2% to 15%. When the enhancing agent is used in the above amounts in accordance with this aspect of the present invention, the after load blood absorbent capacity of the mixture of treated fibers and superabsorbent particles is preferably at least 1.3 times the after load blood absorbent capacity for the mixture of untreated fibers and superabsorbent particles. Using excessive amounts of enhancing agent can introduce unnecessary expense into the coating process. High percentages of enhancing agent can also cause processing problems because the enhancing agent material transfers to equipment surfaces. Therefore, it is often preferred to use no more enhancing agent than is required to enhance the blood absorbent properties of the absorbent composition.

In accordance with this aspect of the present invention, thermoplastic enhancing agents also may be used to help enhance the blood absorbence properties of the superabsorbent composition. The enhancing agent that has the hydrogen bonding or optional the coordinate covalent bonding functionalities itself may be thermoplastic or meltable. The polymeric enhancing agents and some non-polymeric enhancing agents of the present invention have the advantage of being thermoplastic solids. Hence, fibers treated in accordance with the present invention can be thermobonded by elevating the fiber temperature above the softening or melting temperature of the enhancing agent to soften the thermoplastic enhancing agent and thermoplastically bind the fibers to each other, and optionally the fibers to the particles.

In accordance with this invention, the enhancing agents may be applied to fibers before, subsequent, or simultaneously with addition of the superabsorbent particles. Simultaneous addition can be accomplished by two separate streams of particles and enhancing agent that are simultaneously directed at a fibrous substrate, or alternatively merged immediately or some time prior to impacting against the substrate.

Combining superabsorbent particles with enhancing agent coated fibers may be performed under conditions that favor formation of hydrogen bonds or coordinate covalent bonds, and discourage formation of covalent bonds. Conditions that favor covalent bonds are those disclosed in U.S. Pat. Nos. 4,412,036 and 4,467,012. Conditions that favor covalent bond formation are also shown in European Patent Applications 440 472 A1; 427 317 A2; 427 316 A2; and 429 112 A2.

Fibers that have high bulk from intrafiber covalent crosslinks are prepared by individualizing the fibers (for example, in a fiberizer) and curing them at an elevated temperature (above 150° C.). Initial application of the enhancing agent on such high-bulk fibers preferably occurs after the curing step, particularly if the enhancing agent is capable of functioning as a crosslinking material. The specific types of enhancing agents disclosed herein that also can crosslink are polyols, polyaldehydes, polycarboxylic acids, and polyamines (polymeric or nonpolymeric enhancing agents with more than one amine group). If such enhancing agents are present during curing, the enhancing agent will be consumed during the curing step to form covalently crosslinked bonds. When this occurs, the enhancing agent is no longer available for hydrogen or coordinate covalent bonding to the superabsorbent materials and enhancement of blood absorbent properties of the superabsorbent composition.

The intrafiber covalent bond forming processes described in the above European publications require formation of an intermediate that then reacts with a hydroxy group on cellulose to form a covalent ester bond. The presence of more than about 20% water by weight in the fibers is believed to interfere with the formation of the intermediate and inhibits covalent bond formation. Hence, in processes that use polycarboxylic acids, polyols and polyamines (which includes both polymeric and nonpolymeric amines having more than one amine group) as enhancing agents in the present invention, the fibers should contain at least 20% water (or 20–50% water) by weight if the particles and enhancing agent are present in the fibers when curing occurs. The water inhibits covalent bond formation, and prevents all of the enhancing agent from being used to form covalent intrafiber crosslinks. Hence, some of the enhancing agent remains available to enhance the blood absorbent properties of the superabsorbent composition.

The enhancing agents of the present invention can be added to the fibers in any convenient manner. One such procedure is to spray the enhancing agent or enhancing agents on a web of the fibers that is conveyed past a sprayer on a conveyor belt. Alternatively, loose fibers may be allowed to fall past a sprayer, or loose fibers may be moved on a conveyor belt past a sprayer. The loose fibers may also be slurried with or immersed in enhancing agent. It is also preferable to roll coat the enhancing agents on the web, particularly if the enhancing agent is viscous. The fibers may also be sprayed or immersed in the enhancing agent. These fibers can, while still wet be combined with the superabsorbent particles.

One method for uniformly coating the fibers with a enhancing agent and adding the particles is shown in U.S. Pat. No. 5,064,689. However, the invention is not limited to any specific mechanism for combining the fiber, enhancing agent and particles.

III. Production of High Bulk Fibers

For the purposes of full disclosure, the following description of the production of high bulk fibers useful in accordance with the present invention is provided. Production of high bulk fibers with intrafiber crosslinks is known in the art. Processes for making such fibers are described in EP 440 472 A1; EP 427 317 A2; EP 427 316 A2; and EP 429 112 A2, as well as U.S. Patent application Ser. No. 07/607,268 filed Oct. 31, 1990, and its published European counterpart. These high bulk fibers may be used in the present invention. Since methods of making high bulk fibers are known, only a brief description of one such process is given below.

A. Overall System

Figure 3:
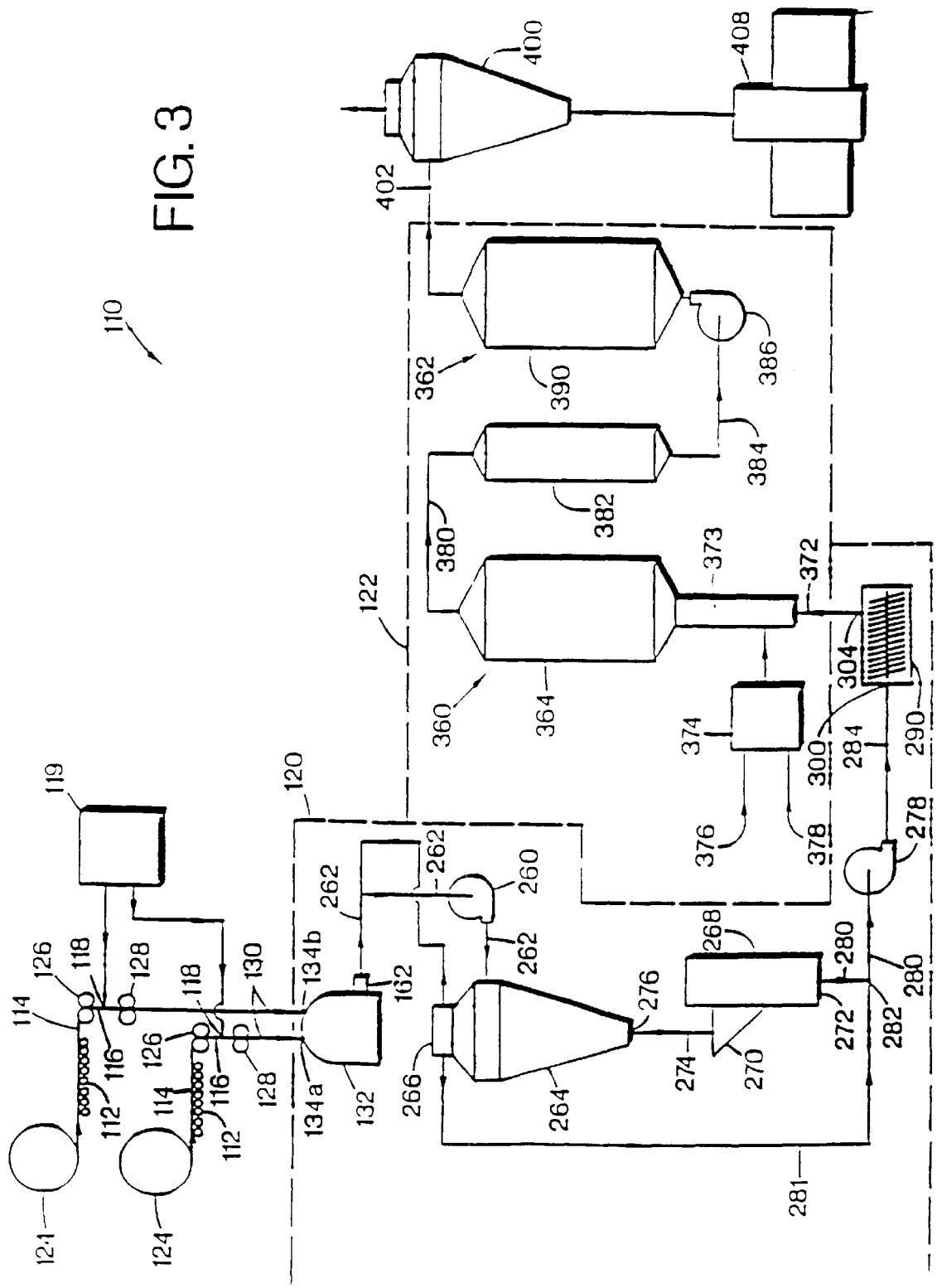
FIG. 3 is a schematic depiction of the components of an apparatus of the present invention that produce high bulk fibers.

Referring to FIG. 3. The apparatus 110 comprises a conveying device 112 for transporting a mat 114 of cellulose fibers or other fibers through a fiber treatment zone 116; an applicator 118 for applying a treatment substance such as a crosslinking substance from a source 119 thereof to the mat 114 at the fiber treatment zone 116; a fiberizer 120 for completely separating the individual cellulose fibers comprising the mat 114 to form a fiber output comprised of substantially unbroken cellulose fibers substantially without nits or knots; and a dryer 122 coupled to the fiberizer for flash evaporating residual moisture from the fiber output and for curing the crosslinking substance, thereby forming dried and cured cellulose fibers.

The mat 114 of cellulose fibers is preferably in an extended sheet form stored in the form of a roll 124 until use. It is normally not necessary that the cellulose fibers comprising the mat 114 be completely dry. Since cellulose is a hydrophilic substance, molecules thereof will typically have a certain level of residual moisture, even after drying. The level of residual moisture is generally 10% wt/wt or less, which is not detectable as "wetness." FIG. 3 also shows that more than one supply, such as multiple rolls 124, of the mat 114 of cellulosic fibers can be simultaneously processed using the present invention.

At the fiber treatment zone 116, sprayers or other applicators 118 apply chemicals such as crosslinking agents to the mat. Typically chemicals are applied uniformly to both sides of the mat. The wetted mat passes between a pair of rollers 128 which assist in distributing the chemicals uniformly through the mat. Other applicators may also, of course, be used.

The crosslinking substance is a liquid solution of any of a variety of crosslinking solutes known in the art. If required, the crosslinking substance can include a catalyst to accelerate the bonding reactions between molecules of the crosslinking substance and cellulose molecules. However, many if not most crosslinking substances do not require a catalyst.

Preferred types of crosslinking substances are selected from a group consisting of urea derivatives such as methylolated urea, methylolated cyclic ureas, methylolated lower alkyl substituted cyclic ureas, methylolated dihydroxy cyclic ureas, and mixtures thereof. A specifically preferred crosslinking substance would be dimethyloldihydroxyethylene urea (DMDHEU). In addition, crosslinking substances can be polycarboxylic acids, such as citric acid. Crosslinking materials are known in the art, such as described in U.S. Pat. No. 3,440,135 to Chung, U.S. Pat. No. 4,935,022 to Lash, et al., U.S. Pat. No. 4,889,595 to Herron, et al., U.S. Pat. No. 3,819,470 to Shaw, et al., U.S. Pat. No. 3,658,613 to Steijer, et al., U.S. Pat. No. 4,822,453 to Dean, et al., and U.S. Pat. No. 4,853,086 to Graef, et al.

Suitable catalysts include acidic salts which can be useful when urea-based crosslinking substances are used. Such salts include ammonium chloride, ammonium sulfate, aluminum chloride, magnesium chloride, or mixtures of these or other similar compounds. Alkali metal salts of phosphorus-containing acids may also be used.

In FIG. 3, the crosslinking substance applied to the mat 114 is obtained from a supply 119 thereof, such as a tank or analogous vessel.

Crosslinked cellulose fibers are individual fibers each comprised of multiple cellulose molecules where at least a portion of the hydroxyl groups on the cellulose molecules have been covalently bonded to hydroxyl groups on neighboring cellulose molecules in the same fiber via crosslinking reactions with extraneously added chemical reagents termed "crosslinking substances" or "crosslinking agents." Suitable crosslinking agents are generally of the bifunctional type which create covalently bonded "bridges" between said neighboring hydroxyl groups.

B. Conveying Device

Referring further to FIG. 3, each mat 114 of cellulosic fibers is conveyed by a conveying device 112, which carries the mats through the fiber treatment zone 116. FIG. 3 also shows a further portion of one type of conveying device comprised of a first pair of rollers 126 and a second pair of rollers 128 for each mat 114. The first and second pair of rollers 126, 128 are particularly effective for urging the corresponding mat at a substantially constant and controlled rate of speed.

C. Fiber Treatment Zone

Each mat 114 is urged by the first and second pair of rollers 126, 128 through the fiber treatment zone 116 where the mat 114 is impregnated with a liquid crosslinking substance. The crosslinking substance is preferably applied to one or both surfaces of the mat using any of a variety of methods known in the art useful for such a purpose, such as spraying, rolling, dipping, or analogous method. Combinations of spray and roller applicators can also be employed.

The crosslinking substance is typically applied in an amount ranging from about 2 kg to about 200 kg chemical per ton of cellulose fiber and preferably about 20 kg to about 100 kg chemical per ton of cellulose fiber.

D. Fiberizer

The next subsystem following the fiber treatment zone is a fiberizer 120 which serves to comminute one or more mats 130 impregnated with the crosslinking substance into individual substantially unbroken cellulose fibers comprising a fiber output.

Referring further to FIG. 3, a first conveyer fan 260 of conventional design can be utilized for propelling the fibers from the outlet 162 of the attrition device 132 through a conduit 262.

An optional component of the fiberizer 120 is a first cyclone 264 or similar apparatus known in the art, utilized in a conventional manner to concentrate the fibers passing out of the outlet 162 of the attrition device 132. The first cyclone 264 receives the fibers through the conduit 262 coupled thereto.

Excess air can be recovered at the top 266 of the first cyclone 264 and recycled as required through a conduit 268 to a location upstream of the first conveyer fan 260 (if used). Such additional air can be beneficial for easing the transfer of the fibers through the first conveyor fan 260.

A disk refiner 268 is another optional component of the fiberizer 120 which can be employed to effect additional separation of fibers (removal of knots) if required. The disk refiner 268 is of a type known in the art and comprises a disk refiner inlet 270 and a disk refiner outlet 272. A representative disk refiner 268 is type DM36 manufactured by Sprout-Bauer, Incorporated of Muncie, Pa. If the disk refiner 268 is used, the inlet 270 thereof is coupled via a conduit 274 to an outlet 276 of the first cyclone 264.

A second conveyor fan 278 may optionally be utilized to urge propagation of the fibers through a conduit 180 downstream of the disk refiner 268. Excess air can be recovered from the top 266 of the first cyclone 264 and routed via a conduit 281 to a tee 282 just upstream of the second conveyor fan 278.

Another optional component of the fiberizer 120 is a fluff generator 290 which receives the fibers from the optional second conveyor fan 278 through a conduit 284. The fluff generator is described in detail below and in copending U.S. Patent application Ser. No. 07/607,157.

E. Dryer

Referring further to FIG. 3, a preferred embodiment of the present apparatus 110 includes a dryer 122 which is utilized to perform two sequential functions: remove residual moisture from the fibers and cure the crosslinking agent. Preferably, the dryer 122 comprises a drying zone 373 for receiving fibers, e.g. from fluff generator outlet 304 and for removing residual moisture from the fibers via a "flash drying" method and a second drying zone 360, 362 for curing the crosslinking agent. In FIG. 3, the curing starts in zone 360 and continues through zone 362.

The FIG. 3 embodiment shows that zone 373 is coupled to the fluff generator outlet by a conduit 372 and to a source 374 of heated air, typically produced by combustion of a supply of natural gas 376 and fresh air 378. The temperature of heated air is regulated to maintain the temperature of the drying zone 373 within a range of about 200° C. to about 315° C. As the fiber output passes into the drying zone 373, the wet fibers comprising the fiber output are substantially instantaneously exposed to the high temperature in this zone. Such rapid exposure to high temperature imparts a "flash drying" effect to the fibers, thereby causing rapid and thorough drying and separation of the fibers. The passage time through the drying zone 373 is preferably less than one second.

The FIG. 3 embodiment shows that the first zone 360 is comprised of a first tower 364 comprised of a body portion 366, an inlet 368, and a first tower outlet 370. The dryer zone 373 is coupled via a conduit 372 to the outlet of the fluff generator 290.

In FIG. 3, the first tower 364 is shown preferably coupled via a conduit 380 to a down tube 382, which is coupled via a conduit 384 to a third conveyor fan 386 located at an inlet 388 of a second tower 390. The third conveyor fan 386 transports the fibers through the dryer which thereby pass into the second tower 390. As the fibers are lofted through the second tower 390, they are still exposed to a curing temperature within a range of about 140° C. to about 180° C., which is sufficient to effect curing of the crosslinking agent without scorching the dry fibers. The lofting keeps the fibers separated until the crosslinking reaction is complete. The curing temperature depends upon the type of crosslinking material used to treat the fibers and also is set at a level so as to not scorch the fibers during curing. It should be noted that single stage dryers may also be used.

The dried and cured fibers exiting the dryer outlet of tower 390 have an extremely low level of nits and virtually no knots. Further, they are not discolored from scorching and the like, and have a median fiber length substantially unchanged from the median length of the fibers comprising the mat 14.

FIG. 3 also shows a second cyclone 400 of conventional design coupled via a conduit 402 to the outlet of tower 390, serving to concentrate the fibers passing therethrough in preparation for collection. The resulting concentrated fibers can be collected using any of a number of collection devices 408 known in the art, such as fiber bagging devices.

IV. Composite Absorbent Products

In accordance with the present invention, absorbent structures or articles may be made from the treated fibers and treated superabsorbent particles. These articles may be composite structures (e.g., made of plural materials). For example, the articles may have a core of plural types of fibers, or fiber layers, with or without covering materials. These products are capable of absorbing significant quantities of blood and other fluids, such as water, urine and other body fluids. Such products include, but are not limited to, sanitary napkins, surgical towels, bandages and the like.

Figure 4:
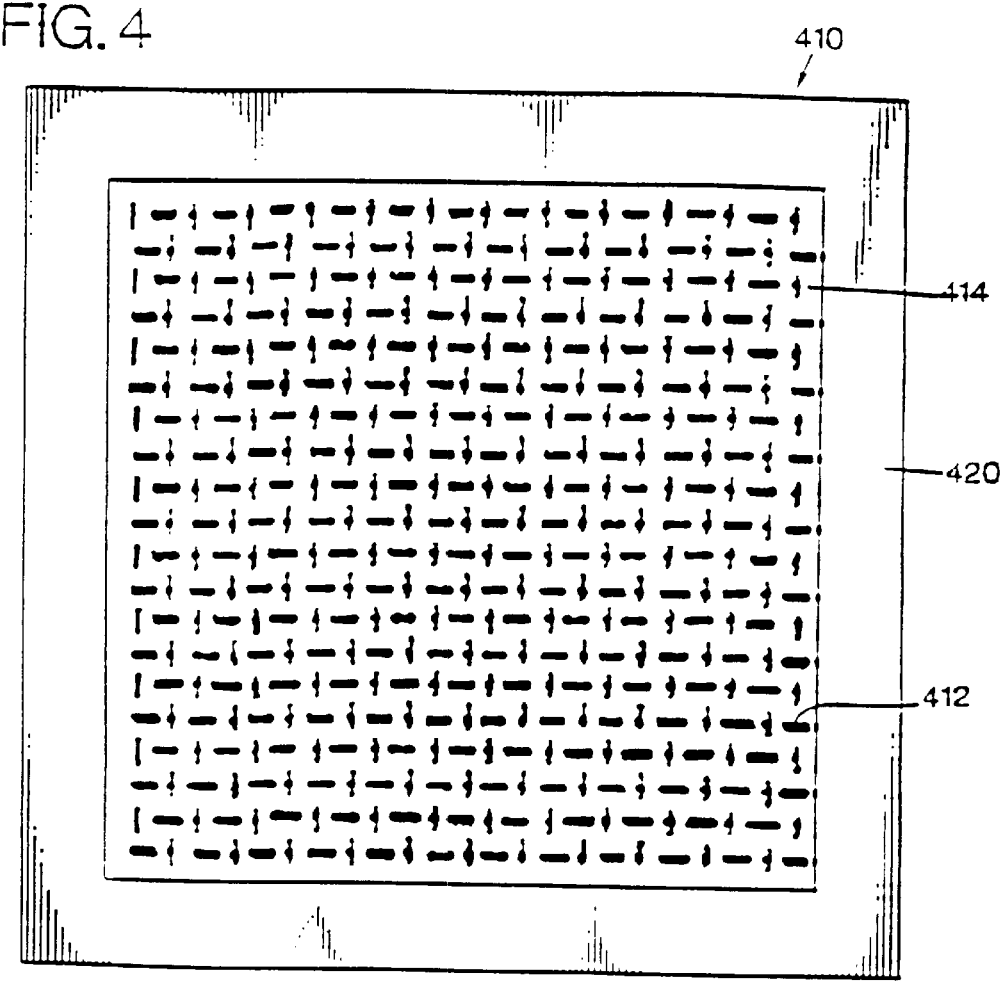
FIG. 4 is a top plan view of a structure into which particles with enhancing agent applied are combined with fibers, the fibers being in the form of an illustrated absorbent pad.
Figure 5:
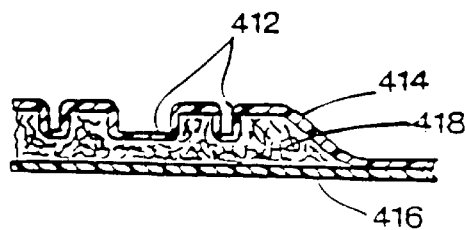
FIG. 5 represents a partial sectional view of the pad of FIG. 4.

FIGS. 4 and 5 illustrate an absorbent pad structure which may be formed from fibers or particles treated with enhancing agent in accordance with the present invention, whether or not they are blended with other fibers or particles. FIGS. 4 and 5 represent an absorbent pad 410 having a heat embossed screen pattern 412. Pads having no pattern may also be used. A pad having a cover sheet 414 and a backing sheet 416 may be formed, for example, by placing a square fiber piece cut from the sheet onto a corresponding precut backing sheet. A corresponding precut cover sheet is placed over the top of the fiber 418 on the backing sheet. This assembly may then be adhesively bonded around a continuous margin 420. Pad 410 can also be formed in many different shapes depending upon its end use.

With reference to FIGS. 6 and 7, an superabsorbent structure in the form of a bandage is shown. A bandage 430 for application to a wound to absorb blood and other bodily fluids is shown. An absorbent pad 440 is securely mounted to an exterior or pad mounting surface 434 of a backing strip 436. Coated fibers 441 and superabsorbent particles or treated superabsorbent particles and fibers are contained in pad 440. Any suitable mounting or securing means may be used to affix pad 440 to the surface 434 of the strip 436. However, it is preferable for surface 434 to be coated with an adhesive so that the pad 440 may be adhesively mounted in place. An exemplary adhesive is ethylene vinyl acetate adhesive. It is also desirable for the overall surface 438 of backing strip 436 to be coated with a conventional adhesive. Surface 438 is the surface which is affixed to the area of the skin surrounding the wound. Conventional "peel-back" tabs may be used to protect the adhesive coating and pad 440 until the bandage is to be applied. This type of backing strip is well known in the art.

The backing strip 436 may be of any known flexible material suitable for application to the skin. It is preferable for the strip 416 to be of a material which is impermeable to the passage of liquid so that fluid from a wound is contained by the bandage. However, the strip 436 may be apertured or otherwise breathable to permit air to reach the wound to promote the healing process. A specific example of a suitable backing strip 436 is a polyethylene film.

The absorbent pad of bandage 430 may also include a cover sheet that is typically made of any suitable material which will readily permit the passage of liquid through the cover sheet to the fibers 441, such as nonwoven fiber webs of fibers such as, for example, rayon, nylon, polyester, propylene and blends thereof. One specifically preferred cover sheet material is a 70 percent rayon/30 percent polyester blend having a basis weight of 18 g/m$^2$ from Scott Paper Company.

Other absorbent articles such as feminine hygiene products, surgical wipes and the like that typically are used to absorb blood or other serous bodily fluid can be formed using the enhancing agent treated fibers or enhancing agent treated superabsorbent particles in accordance with the present invention.

The following examples are provided in order to further describe the present invention and illustrate the enhanced blood absorbency properties achieved by the fibers and particles of the present invention.

V. EXAMPLES

A. Enhancing Agent on Superabsorbent Material

Example 1

The following example illustrates the enhancement of the blood absorbent properties, e.g., free swell blood absorbent capacity and after load blood absorbent capacity of a superabsorbent particle treated with an enhancing agent in accordance with the present invention.

A five gram aliquot of a starch graft polyacrylate hydrogel superabsorbent available from Hoechst-Celanese of Portsmouth, Va., as product designation IM 3900 were suspended in a rapidly mixing Waring blender. Drops of glycerin were added to the suspension in amounts sufficient to produce addition levels of 0.1%, 0.5% and 2.0% of the total weight of the superabsorbent material and the added glycerin. Mixing was continued for 15 seconds before stopping the blender and removing the contents. The resulting materials were then tested for free swell blood absorbent capacity and after load blood absorbent capacity as described below.

An approximately 0.2 gram sample (determined to the fourth decimal place on an analytical balance) was taken from each mixture and sealed in a heat sealable, liquid permeable nonwoven envelope in the form of a tea bag available from Dexter of Windsor Locks, Conn. The samples were then, each in turn, immersed in fresh defibrinated ovine blood (available from Becton Dickinson of Hunt Valley, Md.) and soaked for 30 minutes. After soaking, the samples were suspended to drain any unbound blood for ten minutes, then weighed. The samples were then placed in a Büchner funnel connected to a vacuum, a rubber dam was placed over the samples, and suction sufficient to place a 1.0 psi load on the samples was applied for five minutes. The load was removed and the samples were reweighed. A free swell blood absorbent capacity, on a grams of blood absorbed per gram of superabsorbent material used, was then calculated for the materials by the following formula:

grams/grams free swell blood absorbent capacity =

$$\frac{\text{(wet sample mass} - \text{wet tea bag mass} - \text{dry absorbent mass)}}{\text{dry mass of absorbent material used}}$$

gm/gm after load blood capacity =

$$\frac{\begin{array}{c}\text{(wet sample mass after load} - \\ \text{wet tea bag mass after load} - \text{dry absorbent mass)}\end{array}}{\text{Dry mass absorbent material used}}$$

The wet tea bag mass and wet tea bag mass after load were determined by weighing a sample tea bag without superabsorbent treated as described above for tea bags containing an superabsorbent sample.

For purposes of comparison, a composite of a starch graft polyacrylate hydrogel superabsorbent available from Hoecht-Celanese under the designation IM 1000 was mixed with a cellulose fiber fluff at least partially coated with glycerin in accordance with Example 5. 30% by weight superabsorbent particles based on the combined weight of the superabsorbent particles and the fibrous material was used. This sample was designated 30% IM 1000/RP fluff. Other comparative samples were prepared using the core material from commercially available catamenial products sold under the name. Another comparative example comprising a wood pulp product available from Weyerhaeuser Company under the designation NB 416 was also evaluated for blood absorbence as described above. A comparative sample of untreated IM 3900 superabsorbent particles was also evaluated. The results are shown in Table I.

TABLE I

| Sample | Free Swell Blood Absorbent Capacity (g/g) (no load) | After Load Blood Absorbent Capacity (g/g) (1.0 psi load) |
|---|---|---|
| 100% IM 3900 | 8.48 | 7.76 |
| 99.9% IM 3900 0.1% glycerin | 31.67 | 24.19 |
| 99.5% IM 3900 0.5% glycerin | 24.63 | 19.72 |
| 98% IM 3900 2.0% glycerin | 20.16 | 15.61 |
| 30% IM 1000/RP fluff | 29.96 | 12.77 |
| Always core | 15.70 | 5.91 |
| NB 416 (no SAP) | 25.57 | 9.47 |

The results indicate that a glycerin enhancing agent applied to IM 3900 superabsorbent particles increases the free swell blood absorbent capacity of the superabsorbent particles at least two times and as much as 3.7 times and the after load blood absorbent capacity by at least two times and as much as 3.1 times compared to the same properties for untreated IM 3900 particles. Surprisingly, the results indicate that the most pronounced enhancement of blood absorbent properties of the tested superabsorbent particles occurs at very low levels of glycerin, and tends to be diminished with increasing glycerin amount.

It is worth noting that comparison between various examples in this application is not appropriate because applicants have found that the blood absorbence properties of the test samples varies greatly with the sample of blood that is used in the test procedure. For each of the described examples, a single sample of blood was used to test the samples for a given example, although different samples of blood were used in different examples.

Example 2

The following example illustrates how enhancing agents other than glycerin, with multiple hydrogen bonding functionality, can also improve the blood absorbent capacity of a IM 3900 superabsorbent particle.

Samples were prepared in accordance with Example 1 with the exception that the particular enhancing agent used was differed. Enhancing agents that were solid were dissolved in a 90% ethanol/10% water solution and the solution was added to the air suspension in the Waring blender in amounts sufficient to provide the desired addition levels. After mixing according to Example 1, the contents were removed and allowed to air dry for one hour, after which they were tested as described in Example 1 with the exception that sample sizes were reduced to approximately 0.1 gms to avoid having tea bag volumes becoming a limiting factor. Again, comparative samples of the Always commercially available catamenial product; 100% IM 3900 superabsorbent particles, and a mixture of 30% by weight IM 1000 and the glycerin coated cellulose fiber fluff of Example 5 were tested for comparative purposes. The results are set forth in Table 2.

TABLE II

| Sample | Free Swell Blood Absorbent Capacity (g/g) (no load) | After Load Blood Absorbent Capacity (g/g) (1.0 psi load) |
|---|---|---|
| 100% IM 3900 | 21.58 | 16.74 |
| 99.5% IM 3900 0.5% dipropylene glycol | 29.94 | 22.56 |
| 99.5% IM 3900 0.5% PEG 200 | 35.32 | 26.48 |
| 99.5% IM 3900 0.5% PEG 400 | 25.40 | 19.11 |
| 99.5% IM 3900 0.5% urea | 26.30 | 21.51 |
| 99.5% IM 3900 0.5% ascorbic acid | 28.64 | 23.56 |
| 99.5% IM 3900 0.5% glycine | 26.09 | 21.13 |
| Always | 18.11 | 9.08 |
| 30% IM 1000/RP fluff | 25.29 | 17.42 |

The results in Table 2 indicate that other chemicals, with multiple hydrogen bonding functionality, also improve the blood absorbent capacity of IM 3900 superabsorbent particles, when applied in a manner described above. Again, the improvement is realized at surprisingly low treatment levels. The observed increase in free swell blood absorbent capacity is as high as 1.39 times the free swell blood absorbent capacity of the untreated superabsorbent particles and as low as 1.18 times the free swell blood absorbent capacity of the untreated samples. The after load blood absorbent capacity is observed to be increased as much as 1.58 times and as little as 1.14 times the after load blood absorbent capacity for the untreated superabsorbent particles.

Example 3

Samples of a starch graft polyacrylate hydrogel superabsorbent particle available from Hoecht-Celanese under the designation IM 1000 were combined with 0.5% glycerin enhancing agent as described in Example 1 and allowed to age for two months under ambient conditions. Another set of samples of the same IM 1000 and 0.5% glycerin enhancing agent were prepared and allowed to age for two months in a dessicator. Similar samples of IM 1000 and 0.5% glycerin enhancing agent were freshly prepared and tested for blood absorbence properties at the same time as the aged samples in order to determine the effect of time on the capacity of the treated materials. Also, samples of a wider range of superabsorbent particles were tested to assess whether blood absorbent capacity improvements were possible with other absorbent particles. The superabsorbent particles tested in this example were as follows:

| Superabsorbent Particle | Source |
| --- | --- |
| IM 1000 | Hoechst-Celanese |
| IM 1000F | Hoechst-Celanese |
| FAVOR 800 | Stockhausen |
| Aqualic | BASF |
| J440 | Sumitomo Seika |
| Aridal 1440 | Chemdal |

In addition, comparative samples of the commercially available Always catamenial product and the 30% IM 1000/RP Fluff composite were tested. The results are shown in Table 3.

TABLE III

| Sample | Free Swell Blood Absorbent Capacity (g/g) (no load) | After Load Blood Absorbent Capacity (g/g) (1.0 psi load) |
| --- | --- | --- |
| IM 1000 + Fresh Ambient | 37.39 | 27.26 |
| IM 1000 + Aged Ambient | 31.44 | 23.67 |
| IM 1000 + Fresh Dessicator | 30.01 | 25.97 |
| IM 1000 + Aged Dessicator | 32.80 | 20.82 |
| 100% IM 1000 | 12.07 | 12.81 |
| 99.5% IM 1000 0.5% glycerin | 14.85 | 13.96 |
| 100% IM 1000F | 19.64 | 16.28 |
| 99.5% IM 1000F 0.5% glycerin | 13.82 | 12.40 |
| 100% Favor 800 | 21.37 | 17.40 |
| 99.5% Favor 800 0.5% glycerin | 22.45 | 18.65 |
| 100% Aqualic | 15.61 | 12.42 |
| 99.5% Aqualic 0.5% glycerin | 13.88 | 11.49 |
| 100% J440 | 12.78 | 12.73 |
| 99.5% J440 0.5% glycerin | 19.67 | 16.44 |
| 100 Aridal 1440 | 25.89 | 18.85 |
| 99.5% Aridal 1440 0.5% glycerin | 29.45 | 23.54 |
| Always | 13.19 | 9.40 |
| 30% IM 1000/RP fluff | 30.55 | 19.29 |

The results indicate that handling and storage of the enhancing agent treated superabsorbent particles in the presence of some humidity yields better blood absorbence properties compared to keeping it bone dry. The treated superabsorbent particles blood absorbence capacities tend to fall off over time, though not nearly down to the levels of the untreated superabsorbent particles. Furthermore, although treatment with the glycerin enhancing agent does not yield improved blood absorbent capacity for all superabsorbent particles, the effect is noted over a wide range of superabsorbent particles that are currently commercially available. The observed increase of the free swell blood absorbent capacity of certain samples is as high as 1.54 times the free swell blood absorbent capacity of the untreated superabsorbent particle. The results show that the after load absorbent capacity for some of the samples increases by as much as 1.29 times the after load blood absorbent capacity of the untreated superabsorbent particle.

Example 4

The following example was carried out to identify an optimum level of addition of a glycerin enhancing agent to a IM 3900 superabsorbent particle and to identify other enhancing agents that would also improve the blood absorbence capacity of superabsorbent particles. Where the enhancing agent was a solid, the samples were prepared in accordance with Example 3. Low levels of the enhancing agent were achieved by diluting the enhancing agent with ethanol and adding a sufficient amount of the solution to obtain the desired addition levels, followed by air drying for one hour. Comparative samples of the Always core and the 30% IM 1000/RP fluff were also prepared. All samples were tested as described in Example 1 and the results are shown in Table 4.

TABLE IV

| Sample | Free Swell Blood Absorbent Capacity (g/g) (no load) | After Load Blood Absorbent Capacity (g/g) (1.0 psi load) |
| --- | --- | --- |
| 100% IM 3900 | 29.80 | 21.16 |
| 99.97% IM 3900 0.03% glycerin | 30.66 | 23.28 |
| 99.93% IM 3900 0.07% glycerin | 32.63 | 24.32 |
| 99.90% IM 3900 0.1% glycerin | 27.46 | 20.02 |
| 99.5% IM 3900 0.5% ammonium citrate | 39.17 | 27.89 |
| 99.5% IM 3900 0.5% p-aminoacrylic acid | 39.17 | 26.16 |
| 99.5% IM 3900 0.5% taurine | 30.87 | 22.02 |
| Always core | 16.29 | 11.40 |
| 30% IM 1000/RP fluff | 29.10 | 14.18 |

The differences in free swell blood absorbent capacity and after load blood absorbent capacity for the samples that comprise 100% IM3900 superabsorbent particles in Examples 1, 2, and 4 illustrate the effect that the blood has on the superabsorbent capacity of the superabsorbent particles. The enhancing agents used in this example include glycerin, ammonium citrate, p-aminosalicylic acid, and taurine.

The results indicate that the optimum range for improving the blood absorbent capacity of the IM 3900 superabsorbent particle by treatment with glycerin enhancing agent lies somewhere in the range of less than 0.1%. The optimum level of enhancing agent for maximization of the blood absorbent properties of a superabsorbent particle depend on a number of factors including the particular superabsorbent particle being treated as well as the enhancing agent. The results also indicate that increases in the free swell blood absorbent capacity and after load blood absorbent capacities can be obtained using ammonium citrate, p-aminosalicylic acid, and taurine as the enhancing agent.

B. Enhancing Agents on Fibrous Material

Example 5

The following example illustrates the results achieved when enhancing agent is applied to a cellulose fiber which is then combined with superabsorbent particles. A sample of southern bleached kraft fluff sheet was passed through a roll coater type glue spreader device set to apply glycerin in the amount of 9% by weight, based on the total weight of the fiber and the glycerin. The fluff was then fiberized in a Fitz hammermill fitted with a 1 in$^2$ square holed screen, collected and stored in a plastic bag. The treated fluff was designated as RP fluff Three 2.23 gram samples of several commercially available superabsorbent particles listed below were blended with three 5.2 gram samples of the RP fluff prepared as described above and air laid into 400 gram per square meter pads in a laboratory pad former. The commercially available superabsorbent particles were:

| Superabsorbent Particle | Source |
| --- | --- |
| IM 1000 | Hoechst-Celanese |
| J440 | Sumitomo Seika |
| IM 1000F | Hoechst-Celanese |
| B65S | Atochem |

For comparative purposes, three 7.4 gram samples of NB 416 a pulp sheet available from Weyerhaeuser Company of Tacoma, Wash. and three 7.4 gram samples of the RP fluff prepared as set forth above were similarly air laid in a laboratory pad former. An approximately 0.2 gram sample (determined to the fourth decimal place on an analytical balance) was then taken from each pad and sealed in a heat sealable, liquid permeable, nonwoven (tea bag available from Dexter, Winsor Locks, Conn.) envelope. For comparative purposes, three approximately 0.2 gram samples of the superabsorbent particles without fluff were sealed in similar envelopes. Also, for comparative purposes, several commercially available catamenial products (e.g., ALWAYS, KOTEX and WHISPER available from Proctor and Gamble) were separated into their respective components and approximately 0.2 gram samples from their superabsorbent core material were sealed in similar envelopes. The samples were then tested as described in Example 1.

The results are shown in Table 5.

TABLE V

| Sample | Free Swell Blood Absorbent Capacity (g/g) (no load) | After Load Blood Absorbent Capacity (g/g) (1.0 psi load) |
| --- | --- | --- |
| 100% IM 1000 | 8.98 | 7.37 |
| 30% IM 1000/RP fluff | 28.11 | 20.89 |
| 100% J440 | 8.16 | 8.56 |
| 30% J440/RP fluff | 25.11 | 18.31 |
| 100% IM 1000F | 13.38 | 9.99 |
| 30% IM 1000F/RP fluff | 27.07 | 13.84 |
| 100% B65S | 8.86 | 8.61 |
| 30% B65S/RP fluff | 26.34 | 15.40 |
| NB 416 (no SAP) | 24.85 | 10.86 |
| RP fluff (no SAP) | 21.83 | 8.68 |
| Always core (30% SAP) | 11.84 | 9.02 |
| Kotex core | 9.13 | 5.78 |
| Whisper core | 12.40 | 9.38 |

The data shown in Table 5 indicates that composites of the RP fluff at least partially coated with the glycerin enhancing agent and superabsorbent particles have superior blood absorbent capacities as compared to superabsorbent particles alone, the RP fluff treated with enhancing agent alone, untreated pulp fibers alone, or the absorbent core material from the commercially available catamenial devices tested. While the free swell blood absorbent capacities of the combination of the superabsorbent particles and the cellulose fibers coated with enhancing agent are similar to the capacities of the cellulose fibers coated with enhancing agent alone (in the free swell case), enhancements of the blood absorbent capacity of the mixture are notable when the samples are exposed to load conditions as structures made with such materials may encounter during actual use (i.e., after load capacity).

Example 6

Samples of an NB 416 pulp sheet available from Weyerhaeuser Company and fibers coated with glycerin enhancing agent (RP fluff) as described in Example 5 were each hammer milled in a Fitz hammer mill fitted with a ⅜ inch diameter round hole screen while superabsorbent IM 1000 particles available from Hoechst-Celanese were simultaneously added in an amount sufficient to produce 30% and 45% by weight of the combined weight of the fibers and the superabsorbent particles. As each material was produced, it was shunted to an M&J air lay machine (available from M&J Horstens, Denmark) and air laid into a 400 gram per square meter web. Samples of each, as well as a core from the commercially available catamenial product Always, were tested as described in Example 1. Results are shown in Table 6.

TABLE VI

| Sample | Free Swell Blood Absorbent Capacity (g/g) (no load) | After Load Blood Absorbent Capacity (g/g) (1.0 psi load) |
| --- | --- | --- |
| 30% IM 1000/NB 416 | 28.78 | 12.56 |
| 30% IM 1000/RP fluff | 29.26 | 16.88 |
| 45% IM 1000/NB 416 | 29.02 | 15.51 |
| 45% IM 1000/RP | 32.19 | 19.43 |
| Always core | 15.10 | 11.78 |

The results in Table 6 do not confirm or disprove the possibility that any composite of superabsorbent particles and untreated fibers might have an superabsorbent capacity for blood similar to that of the enhancing agent treated fibers and superabsorbent particle composites. The results shown in Table 6 show a marginal increase in capacity for the enhancing agent fiber/superabsorbent composites in the no-load case (free swell blood absorbent capacity) and, a more marked increase in the after load (after load blood absorbent capacity) results.

While the preferred embodiment of the invention has been illustrated and described, it will be appreciated that various changes can be made therein without departing from the spirit and scope of the invention. It should be understood that the foregoing examples are provided to exemplify specific embodiments of the present invention that are not intended to limit the scope of the present invention.

The embodiments of the invention in which an exclusive property or privilege is claimed are defined as follows:

1. A modified superabsorbent material for absorbing blood, comprising:

a superabsorbent material; and an enhancing agent applied to the superabsorbent material as a liquid for increasing the blood absorbence properties of the superabsorbent material, the enhancing agent being propylene glycol and being at least partially bonded to the superabsorbent material through hydrogen bonds or coordinate covalent bonds in the absence of covalent bonds between the enhancing agent and the superabsorbent material, and the enhancing agent being present in an amount ranging from about 0.01% to 10% of the total weight of the superabsorbent material.

2. The modified superabsorbent material of claim 1, wherein the enhancing agent is present in an amount ranging from about 0.01 to about 9.0% of the total weight of the superabsorbent material.

3. The modified superabsorbent material of claim 1, wherein the enhancing agent is present in an amount ranging from about 0.01 to about 8.0% of the total weight of the superabsorbent material.

4. The modified superabsorbent material of claim 1, wherein the enhancing agent is present in an amount ranging from about 0.01 to about 3.0% of the total weight of the superabsorbent material.

5. A modified superabsorbent material for absorbing blood, comprising:

a superabsorbent material; and an enhancing agent applied to the superabsorbent material as a liquid for increasing the blood absorbence properties of the superabsorbent material, the enhancing agent being ethylene glycol and being at least partially bonded to the superabsorbent material through hydrogen bonds or coordinate covalent bonds in the absence of covalent bonds between the enhancing agent and the superabsorbent material, and the enhancing agent being present in an amount ranging from about 0.01% to 10% of the total weight of the superabsorbent material.

6. The modified superabsorbent material of claim 5, wherein the enhancing agent is present in an amount ranging from about 0.01 to about 9.0% of the total weight of the superabsorbent material.

7. The modified superabsorbent material of claim 5, wherein the enhancing agent is present in an amount ranging from about 0.01 to about 8.0% of the total weight of the superabsorbent material.

8. The modified superabsorbent material of claim 5, wherein the enhancing agent is present in an amount ranging from about 0.01 to about 3.0% of the total weight of the superabsorbent material.

9. A modified superabsorbent material for absorbing blood, comprising:

a superabsorbent material; and an enhancing agent applied to the superabsorbent material as a liquid for increasing the blood absorbence properties of the superabsorbent material, the enhancing agent being butylene glycol and being at least partially bonded to the superabsorbent material through hydrogen bonds or coordinate covalent bonds in the absence of covalent bonds between the enhancing agent and the superabsorbent material, and the enhancing agent being present in an amount ranging from about 0.01% to 10% of the total weight of the superabsorbent material.

10. The modified superabsorbent material of claim 9, wherein the enhancing agent is present in an amount ranging from about 0.01 percent to about 9.0% of the total weight of the superabsorbent material.

11. The modified superabsorbent material of claim 9, wherein the enhancing agent is present in an amount ranging from about 0.01 to about 8.0% of the total weight of the superabsorbent material.

12. The modified superabsorbent material of claim 9, wherein the enhancing agent is present in an amount ranging from about 0.01 to about 3.0% of the total weight of the superabsorbent material.

13. A modified superabsorbent material for absorbing blood comprising:

a superabsorbent material; and an enhancing agent applied to the superabsorbent material as a liquid for increasing the blood absorbence properties of the superabsorbent material, the enhancing agent being a diol and being at least partially bonded to the superabsorbent material through hydrogen bonds or coordinate covalent bonds in the absence of covalent bonds between the enhancing agent and the superabsorbent material, and the enhancing agent being present in an amount ranging from about 0.01% to 10% of the total weight of the superabsorbent material.

14. The modified superabsorbent material of claim 13, wherein the enhancing agent is present in an amount ranging from about 0.01 to about 9.0% of the total weight of the superabsorbent material.

15. The modified superabsorbent material of claim 13, wherein the enhancing agent is present in an amount ranging from about 0.01 to about 8.0% of the total weight of the superabsorbent material.

16. The modified superabsorbent material of claim 13, wherein the enhancing agent is present in an amount ranging from about 0.01 to about 3.0% of the total weight of the superabsorbent material.

* * * * *

UNITED STATES PATENT AND TRADEMARK OFFICE
CERTIFICATE OF CORRECTION

PATENT NO. : 6,395,395 B1  
DATED : May 28, 2002  
INVENTOR(S) : M.R. Hansen et al.

Page 1 of 2

It is certified that error appears in the above-identified patent and that said Letters Patent is hereby corrected as shown below:

<u>Title page,</u>  
Item [63], Related U.S. Application Data,

"Continuation of application No. 08/675,803, filed on Jul. 5, 1996, which is a continuation of application No. 08/181,494, filed on Jan. 12, 1994, which is a continuation-in-part of application No. 07/931,059, filed on Aug. 17, 1992, now Pat. No. 5,543,215, which is a continuation-in-part of application No. 07/931,277, filed on Aug. 17, 1992, now Pat. No. 5,538,783, which is a continuation-in-part of application No. 07/931,213, filed on Aug. 17, 1992, now Pat. No. 5,300,192, which is a continuation-in-part of application No. 07/931,278, filed on Aug. 17, 1992, now Pat. No. 5,352,480, which is a continuation-in-part of application No. 07/931,284, filed on Aug. 17, 1992, now Pat. No. 5,308,896, which is a continuation-in-part of application No. 07/931,279, filed on Aug. 17, 1992, now Pat. No. 5,589,256, which is a continuation-in-part of application No. 08/107,469, filed on Aug. 17, 1993, now Pat. No. 5,672,418, which is a continuation-in-part of application No. 08/108,219, filed on Aug. 17, 1993, now Pat. No. 5,607,759, which is a continuation-in-part of application No. 08/107,467, filed on Aug. 17, 1993, now Pat. No. 5,693,411, which is a continuation-in-part of application No. 08/108,218. filed on Aug. 17, 1993, now Pat. No. 5,641,561, which is a continuation-in-part of application No. 08/153,819, filed on Nov. 15, 1993, now Pat. No. 5,447,997, which is a continuation-in-part of application No. 08/108,217 filed on Aug. 17, 1993, now Pat. No. 5,547,745."

should read

--Continuation of application No. 08/675,803, filed Jul. 5, 1996, now Pat. No. 5,998,032, which is a continuation of application No. 08/181,494, filed Jan. 12, 1994, now abandoned; which is a continuation in-part of application No. 07/931,059, filed on Aug. 17 1992, now Pat. No. 5,543,215; application No. 07/931,277, filed on Aug. 17, 1992, now Pat. No. 5,538,783; application No. 07/931,213, filed on Aug. 17, 1992, now Pat. No. 5,300,192; application No. 07/931,278, filed on Aug. 17, 1992, now Pat. No. 5,352,480; application No. 07/931,284, filed on Aug. 17, 1992, now Pat. No. 5,308,896; application No. 07/931,279, filed on Aug. 17, 1992, now Pat. No. 5,589,256; application No. 08/107,469, filed on Aug. 17, 1993, now Pat. No. 5,672,418; application No. 08/108,219, filed on Aug. 17, 1993, now Pat. No. 5,607,759; application No. 08/107,467, filed on Aug. 17, 1993, now Pat. No. 5,693,411; application No. 08/108,217, filed on Aug. 17, 1993, now Pat.

UNITED STATES PATENT AND TRADEMARK OFFICE
CERTIFICATE OF CORRECTION

PATENT NO.    : 6,395,395 B1
DATED         : May 28, 2002
INVENTOR(S)   : M.R. Hansen et al.

It is certified that error appears in the above-identified patent and that said Letters Patent is hereby corrected as shown below:

Related U.S. Application Data cont'd,

No. 5,547,745; application No. 08/108,218, filed on
Aug. 17, 1993, now Pat. No. 5,641,561; and
application No. 08/153,819, filed on Nov. 15, 1993,
now Pat. No. 5,447,997.--

Signed and Sealed this

Eighteenth Day of March, 2003

JAMES E. ROGAN
*Director of the United States Patent and Trademark Office*